US011730551B2

(12) United States Patent
Kaiser

(10) Patent No.: US 11,730,551 B2
(45) Date of Patent: Aug. 22, 2023

(54) STEERABLE MEDICAL DEVICE WITH STRAIN RELIEF ELEMENTS

(71) Applicant: CANON U.S.A., INC., Melville, NY (US)

(72) Inventor: Christopher Charles Kaiser, Cambridge, MA (US)

(73) Assignee: Canon U.S.A., Inc., Melville, NY (US)

( * ) Notice: Subject to any disclaimer, the term of this patent is extended or adjusted under 35 U.S.C. 154(b) by 352 days.

(21) Appl. No.: 17/176,676

(22) Filed: Feb. 16, 2021

(65) Prior Publication Data

US 2021/0259790 A1 Aug. 26, 2021

Related U.S. Application Data

(60) Provisional application No. 63/045,643, filed on Jun. 29, 2020, provisional application No. 62/980,927, filed on Feb. 24, 2020.

(51) Int. Cl.
*A61B 34/30* (2016.01)
*A61B 17/00* (2006.01)
(Continued)

(52) U.S. Cl.
CPC ........ *A61B 34/30* (2016.02); *A61B 17/00234* (2013.01); *A61B 1/0055* (2013.01);
(Continued)

(58) Field of Classification Search
CPC . A61B 1/00114; A61B 1/0052; A61B 1/0055; A61B 1/0057; A61B 17/00234;
(Continued)

(56) References Cited

U.S. PATENT DOCUMENTS 5,383,923 A 1/1995 Webster, Jr.
5,702,433 A 12/1997 Taylor et al.
(Continued)

FOREIGN PATENT DOCUMENTS

JP H6-327629 A 11/1994
JP H8-224244 A 9/1996
(Continued)

OTHER PUBLICATIONS

Hu, X. et al., "Steerable catheters for minimally invasive surgery: a review and future directions", Computer Assisted Surgery, 2018, pp. 21-41, vol. 23, No. 1.

*Primary Examiner* — Mohamed G Gabr
(74) *Attorney, Agent, or Firm* — Canon U.S.A., Inc., IP Division

(57) ABSTRACT

A steerable medical instrument, such as a catheter or endoscope, comprises a tubular body having non-steerable section and steerable sections arranged from a proximal end to a distal end thereof. The tubular body defines a tool channel and a plurality of wire conduits formed along the wall of the tubular body. The steerable section includes wire-guiding members arranged in lengthwise direction alternated with void regions. A control wire arranged in a first conduit within the wall of the tubular body is connected to an actuator and transfers an actuating force to bend the steerable section. An electrical cable arranged along the wall of the tubular body has strain relief elements. The strain relief elements are portions of the cable arranged in at least one void region and configured to freely move within the void regions to provide strain relief to the electrical cable when the tubular body bends.

25 Claims, 18 Drawing Sheets

(51) Int. Cl.
  *A61B 1/005* (2006.01)
  *A61M 25/00* (2006.01)
  *A61M 25/01* (2006.01)
(52) U.S. Cl.
  CPC ..... *A61B 1/0057* (2013.01); *A61B 2017/0034* (2013.01); *A61B 2017/00314* (2013.01); *A61B 2017/00327* (2013.01); *A61M 25/0054* (2013.01); *A61M 25/0113* (2013.01); *A61M 2025/0098* (2013.01)
(58) Field of Classification Search
  CPC ........... A61B 2017/00314; A61B 2017/00323; A61B 2017/00327; A61B 2017/0034; A61B 2034/301; A61B 34/30; A61B 34/71; A61M 2025/0098; A61M 25/0054; A61M 25/0113; A61M 25/0138; A61M 25/0147
  See application file for complete search history.

(56) References Cited

U.S. PATENT DOCUMENTS

| | | | |
|---|---|---|---|
| 5,897,488 | A | 4/1999 | Ueda |
| 6,249,708 | B1 | 6/2001 | Nelson et al. |
| 6,626,852 | B2 | 9/2003 | White et al. |
| 6,991,616 | B2 | 1/2006 | Bencini et al. |
| 9,144,370 | B2 | 9/2015 | Kato et al. |
| 99,134,573 | | 3/2018 | Banik et al. |
| 10,405,774 | B2 | 9/2019 | Wilczyniski et al. |
| 10,416,247 | B2 | 12/2019 | Govari et al. |
| 2001/0037073 | A1* | 11/2001 | White .................. A61B 8/12 600/459 |
| 2002/0080233 | A1 | 7/2002 | Irion et al. |
| 2002/0188226 | A1 | 12/2002 | White et al. |
| 2005/0131279 | A1* | 6/2005 | Boulais ............. A61B 1/00071 600/141 |
| 2005/0274425 | A1 | 12/2005 | Ostrander et al. |
| 2007/0135803 | A1 | 6/2007 | Belson |
| 2007/0151390 | A1 | 7/2007 | Blumenkranz et al. |
| 2013/0023859 | A1 | 1/2013 | Malkowski |
| 2014/0069683 | A1 | 3/2014 | Tanaka et al. |
| 2015/0088161 | A1 | 3/2015 | Hata et al. |
| 2018/0153381 | A1 | 6/2018 | Wei et al. |
| 2018/0192854 | A1 | 7/2018 | Hata et al. |
| 2018/0243900 | A1 | 8/2018 | Tanaka et al. |
| 2018/0311006 | A1 | 11/2018 | Kose et al. |
| 2019/0015978 | A1 | 1/2019 | Takagi et al. |
| 2019/0105468 | A1 | 4/2019 | Kato et al. |
| 2019/0285868 | A1 | 9/2019 | Haraguchi et al. |
| 2020/0179661 | A1 | 6/2020 | Fischell et al. |

FOREIGN PATENT DOCUMENTS

| | | |
|---|---|---|
| JP | 2008-509785 A | 4/2008 |
| JP | 2019-93119 A | 6/2019 |
| JP | 2019-531807 A | 11/2019 |
| WO | 2016/199472 A1 | 12/2016 |
| WO | 2018204202 A1 | 11/2018 |
| WO | 2020/086749 A1 | 4/2020 |
| WO | 2020/092096 A1 | 5/2020 |
| WO | 2020/092097 A1 | 5/2020 |

* cited by examiner

FIG. 4B1

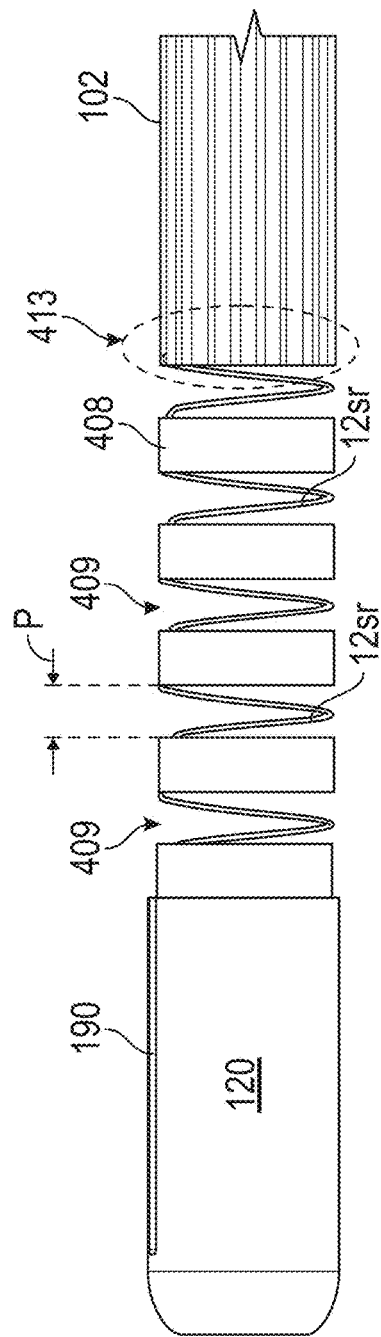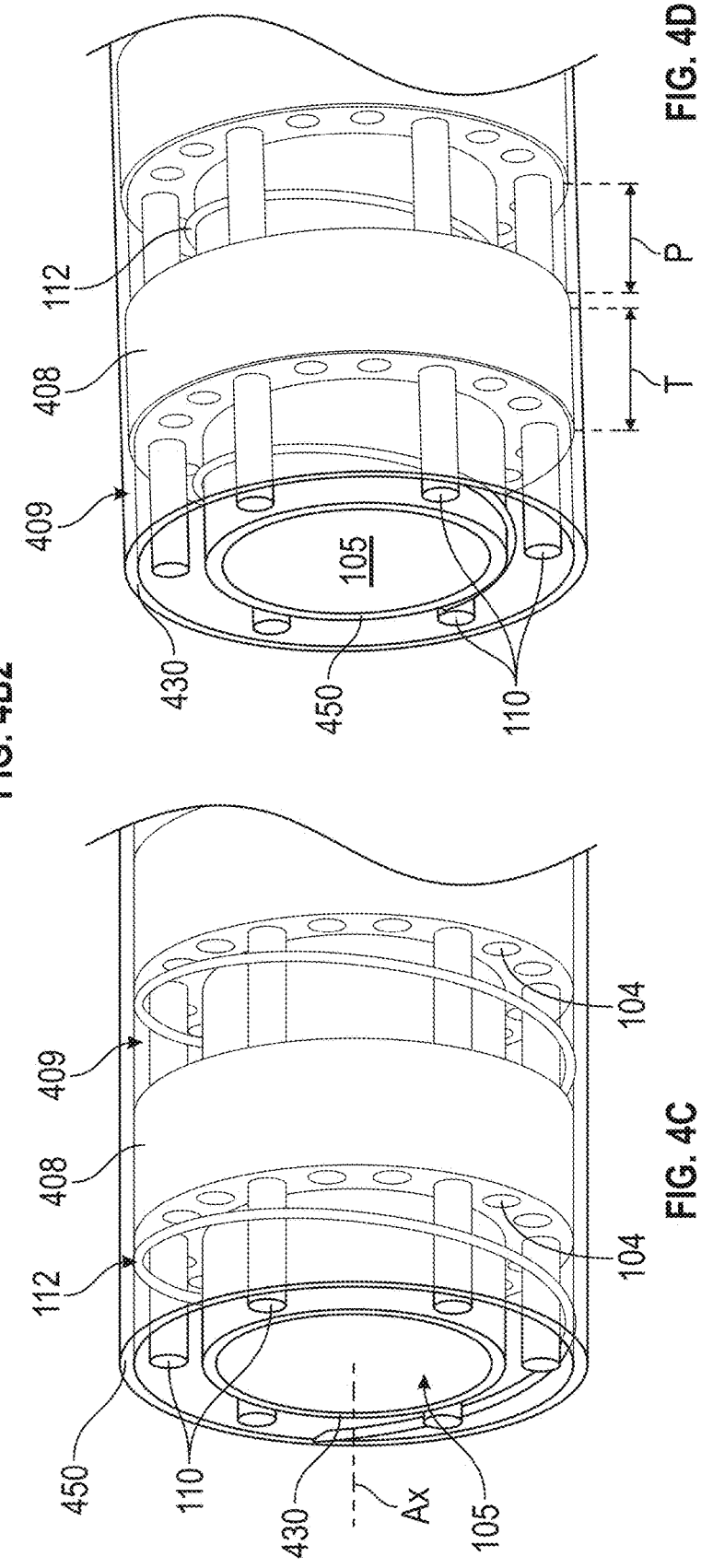

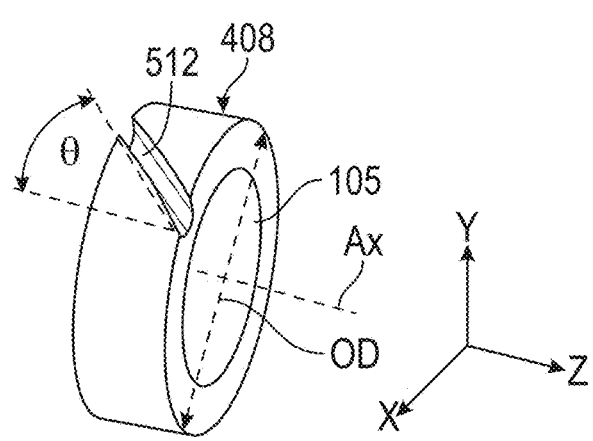
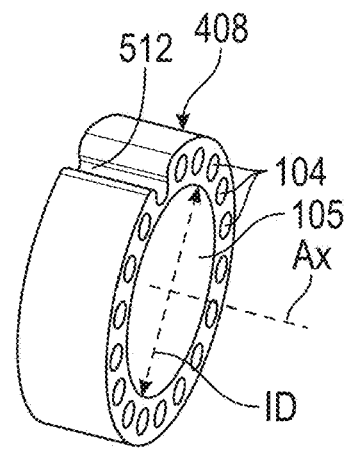
FIG. 6A  FIG. 6B
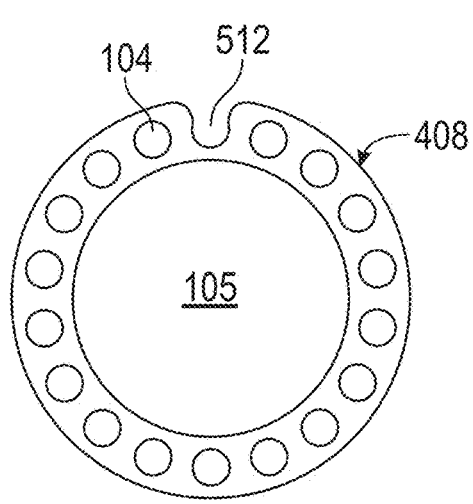
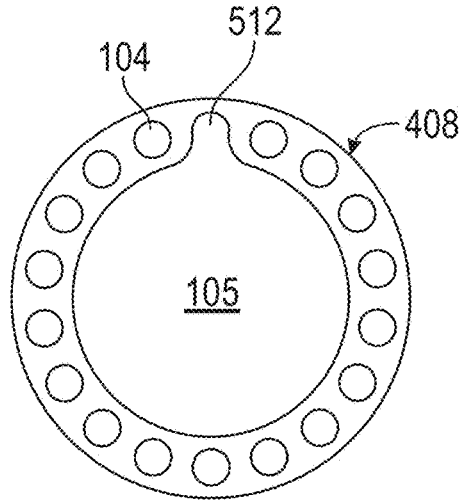
FIG. 6C  FIG. 6D
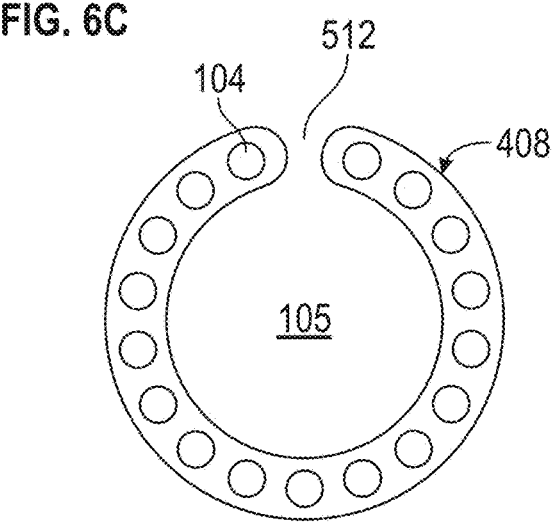
FIG. 6E

FIG. 12B         INSET A

STEERABLE MEDICAL DEVICE WITH STRAIN RELIEF ELEMENTS

CROSS-REFERENCE TO RELATED APPLICATIONS

The present application claims priority to U.S. provisional applications No. 62/980,927 filed Feb. 24, 2020 and No. 63/045,643 filed Jun. 29, 2020. The disclosures of the above-listed provisional applications are hereby incorporated by reference in their entirety for all purposes. Priority benefit is claimed under 35 U.S.C. § 119(e).

BACKGROUND INFORMATION

Field of Disclosure

The present disclosure generally relates to steerable medical devices. More particularly the present disclosure exemplifies various embodiments of a steerable medical device having cable strain relief elements. The steerable medical device is applicable to interventional medical tools and instruments, such as endoscopes and catheters, configured to navigate through intraluminal tortuous paths under manual and/or robotic control.

Description of Related Art

Bendable medical instruments such as endoscopes and catheters generally include an elongated flexible tubular shaft commonly referred to as a sleeve or sheath guide, which has a cylindrical opening extending from a proximal end to a distal end. One or more tool channels extend along (typically inside) the cylindrical opening to allow access to end effectors located at the distal end of the sheath. In addition to end effectors, endoscopes and catheters typically include imaging, illumination, and sensing components at the distal end of the flexible shaft to enable safe navigation through non-linear lumens or tortuous pathways within the body of a patient. This type of medical instrument is configured to provide flexible access to target areas while retaining torsional and longitudinal rigidity so that physicians can control the end effectors located and imaging devices at the distal end by maneuvering dial wheels, control knobs, or joystick controllers a proximal end of the instrument.

Steerable medical instruments transfer motions of the hands of a user (such as an endoscopist) from a handle of the instrument to the distal end of the sheath using one or more long and flexible cables, which are attached to actuating elements on the handle side and to one or more joint mechanisms at the distal end of the sheath. This is similar to transferring motions from a muscle of a human body to a joint through a tendon. Accordingly, in steerable medical instruments, actuation of the joint mechanisms by the cable is also referred to as tendon-driven actuation. To improve accuracy of tendon-driven actuation, ensure safety and minimize patient trauma or discomfort, robotically controlled actuation and image guided operation of steerable instrument is preferred.

There is a wide variety of robots applicable to steerable medical devices, and all robots use a mechanical structure of several links and actuators to operate the cables and joints with one or more degrees of freedom of motion. The actuators driving the tendon cables may include a variety of different types of mechanisms capable of applying a force to a tendon, e.g., electromechanical motors, pneumatic and hydraulic cylinders, pneumatic and hydraulic motors, solenoids, shape memory alloy (SMA) wires, electronic rotary actuators or other devices or methods as known in the art. An example of such robotic controlled instrument is the Da Vinci Surgical System made by Intuitive Surgical Inc.

Frequently, robotically controlled intraluminal steerable instruments, such as catheters and endoscopes, incorporate a number of different electronic components. These components typically have electrical wiring which gets routed internally through the wall of the tubular shaft. The electrical wiring cables can be routed such that they are offset from the instrument's central axis. In such a design, when the steerable instrument takes on a curved geometry, the length of wire required to adapt to that geometry becomes longer than the original wire length. This creates a strain condition on the electrical cable which in turn can negatively impact catheter maneuverability and may damage the electrical cable itself.

The current state of the art provides cable strain relief designs that have substantial contact with other structures of the catheter body, where the electrical wiring is disposed within a cable lumen with geometries that limit functionality. See, for example, patent and pre-grant patent application publications including U.S. Pat. Nos. 5,897,488 A1, 10,405,774 B2, US 2001/0037073 A1, US 2002/0080233 A1, and US 2018/0153381 A1. In particular, U.S. Pat. No. 5,897,488 describes the use of coiled wire designed and configured to take on and maintain states of stress. However, what is necessary is for the instrument to adapt to different geometrical conditions and maintain states of minimal or non-stress. On the other hand, U.S. patent Ser. No. 10/405,774 describes an elongate probe with wires/cable coiled around the body of the probe; these coiled wires function as a position sensor, and have substantial contact with other structures of the probe such that the coiled wires experience stress and contribute to increased tension of the probe during manipulation.

Therefore, there is a need for an improved steerable medical instrument having improved flexibility (or rigidity) for efficiently traveling through tortuous paths without causing pain or discomfort to a patient and without causing excessive strain in the delicate electrical wiring embedded within the tubular shaft of the steerable instrument.

SUMMARY OF EXEMPLARY EMBODIMENTS

According to at least one embodiment of this disclosure, there is provided a robotically steerable medical instrument, such as an endoscope or a catheter, comprising an elongate tubular body having a longitudinal axis, a proximal end, a distal end, and a plurality of channels arranged along the wall of the tubular body, the tubular body having a non-steerable section and a steerable section. The steerable section includes ring-shaped wire-guiding members arranged in a lengthwise direction alternated with void regions. Control wires are arranged along the wall of the tubular body and connected to an actuator to cause a distal portion of the tubular body to bend at an angle with respect to the longitudinal axis. An electrical cable also arranged along the wall of the tubular body has strain relief elements arranged in at least one void region; the strain relief elements are configured to provide strain relief to the electrical cable when the tubular body bends. In one embodiment, the strain relief elements are portions of the electrical cable loosely arranged in one or more void regions either coiled or wrapped around the tool channel. In this case, the electrical cable can be routed above the control wires, below the control wires, or alternately above and below the control wires. In another embodiment, the strain relief elements are portions of the electrical cable folded in an "S" or "C" shape (or other shapes) loosely arranged in one or more void regions in a lengthwise direction next to the control wires no, but without coming into contact with control wire no.

According to one embodiment, a steerable medical instrument (100) comprises: an elongate tubular body having a longitudinal axis, a proximal end, a distal end, and a plurality of channels arranged along the wall of the tubular body, the tubular body having a non-steerable section and at least one steerable section; a control wire (110) arranged in a first channel (104) within the wall of the tubular body and extending through the non-steerable section and through the at least one steerable section, the control wire having a first end attached to the at least one steerable section and a second end connected to an actuator which causes the control wire to slide along the first channel so as to bend the tubular body at an angle with respect to the longitudinal axis; and an electrical cable (112) arranged in a second channel (104) within the wall of the tubular body and extending through the non-steerable section (102) and through the at least one bendable section (101), the electrical cable having a first end fixed to the at least one bendable section and a second end secured to power source terminal (212) of the medical instrument, wherein the electrical cable has a strain relief portion (12sr) configured to provide an amount of slack, such that the electrical cable does not slide along the second channel when the tubular body bends at an angle with respect to the longitudinal axis.

According to one embodiment of the medical instrument, the second channel in which the electrical cable is arranged has a circular cross section. According to one embodiment of the medical instrument, the second channel in which the electrical cable is arranged has a non-circular cross section.

According to one embodiment of the medical instrument, the non-steerable section of the catheter body includes a tubular shaft having the plurality of conduits arranged along the wall of the shaft, and the steerable section of the catheter body includes a plurality of ring-shaped wire-guiding members arranged at a predetermined distance from each other distally to the tubular shaft, and the plurality of wire-guiding members are arranged concentric to the longitudinal axis of the instrument so as to form a plurality of void regions arranged alternately with the wire-guiding members.

According to one embodiment of the medical instrument, the strain relief portions (12sr) include a portion of the electrical cable which is folded (coiled) in an "S" shape or "C" shape in each void region (409) of the catheter body. According to one embodiment of the medical instrument, the strain relief portions (12sr) includes a portion of the electrical cable wrapped around the tool channel and above and/or below the control wire (110) in each void region (409).

In at least one embodiment of the medical instrument, the wire-guiding members measure 1 mm in length and are arranged at intervals of 0.5 to 1 mm length. The length is measured in the lengthwise direction of the catheter body. Moreover, the plurality of wire-guiding members each includes a plurality of through holes or wire conduits to pass therethrough a control wire, and at least one wire conduit to guide therethrough the electrical cable.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objectives, features and advantages of the present disclosure will become apparent from the following description when taken in conjunction with the accompanying figures showing illustrative embodiments of the present disclosure.

FIG. 4A, FIG. 4B1, FIG. 4B2, FIG. 4C, and FIG. 4D, illustrate various details of a strain relief design for a portion of an electrical cable 112 arranged in the steerable section 103 of the steerable instrument 100, according to a first embodiment.

FIG. 6A, FIG. 6B, FIG. 6C, FIG. 6D, and FIG. 6E show various details of wire-guiding members 408.

FIG. 12A, FIG. 12B, and FIG. 12C are photographs of a prototype steerable instrument 100 built according to strain relief designs of the second embodiment disclosed herein.

DETAILED DESCRIPTION OF EXEMPLARY EMBODIMENTS

Figure 1A:
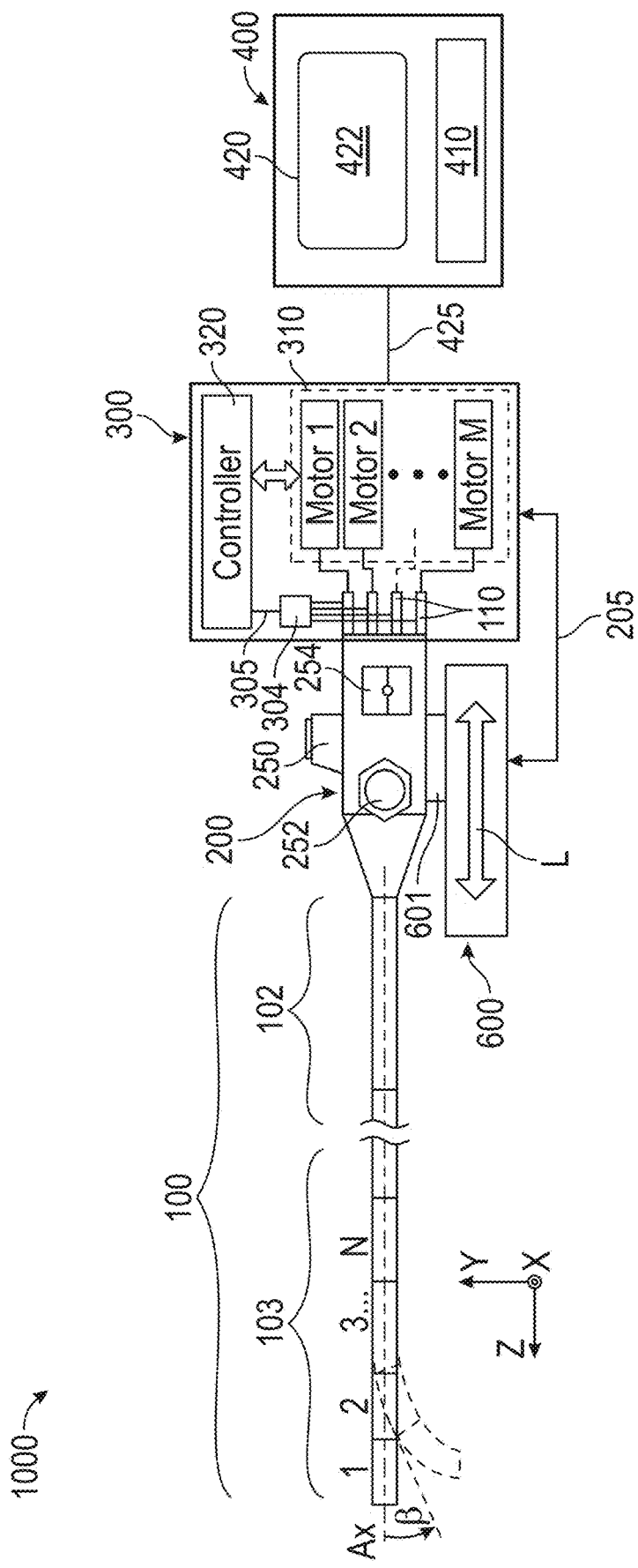
FIG. 1A illustrates a general structure of a continuum robot system 1000 configured to control a steerable instrument 100, according to one embodiment of the present disclosure.

Throughout the figures, the same reference numerals and characters, unless otherwise stated, are used to denote like features, elements, components or portions of the illustrated embodiments. In addition, while the subject disclosure is described in detail with reference to the enclosed figures, it is done so in connection with illustrative exemplary embodiments. It is intended that changes and modifications can be made to the described exemplary embodiments without departing from the true scope and spirit of the subject disclosure as defined by the appended claims. Although the drawings represent some possible configurations and approaches, the drawings are not necessarily to scale and certain features may be exaggerated, removed, or partially sectioned to better illustrate and explain certain aspects of the present disclosure. The descriptions set forth herein are not intended to be exhaustive, exclusive, or otherwise limit or restrict the claims to the precise forms and configurations shown in the drawings and disclosed in the following detailed description.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without limitation and without departing from structural or functional meaning.

As used herein, the singular forms "a", "an", and "the" are intended to include the plural forms as well, unless the context clearly indicates otherwise. It should be further understood that the terms "includes" and/or "including", "comprises" and/or "comprising", "consists" and/or "consisting" when used in the present specification and claims, specify the presence of stated features, integers, steps, operations, elements, and/or components, but do not preclude the presence or addition of one or more other features, integers, steps, operations, elements, components, and/or groups thereof not explicitly stated. Further, in the present disclosure, the transitional phrase "consisting of" excludes any element, step, or component not specified in the claim. It is further noted that some claims or some features of a claim may be drafted to exclude any optional element; such claims may use exclusive terminology as "solely," "only" and the like in connection with the recitation of claim elements, or it may use of a "negative" limitation.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−13.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to include all sub-ranges subsumed therein. As used herein, the term "substantially" is meant to allow for deviations from the descriptor that do not negatively affect the intended purpose. For example, deviations that are from limitations in measurements, differences within manufacture tolerance, or variations of less than 5% can be considered within the scope of substantially the same. The specified descriptor can be an absolute value (e.g. substantially spherical, substantially perpendicular, substantially concentric, etc.) or a relative term (e.g. substantially similar, substantially the same, etc.).

The present disclosure generally relates to medical devices, and exemplifies embodiments of robotically controlled steerable instrument which may be applicable to an endoscope (e.g., a bronchoscope), or a catheter for optical coherence tomographic (OCT) or intravascular ultrasound (IVUS), or a combination of such apparatuses (e.g., a multi-modality optical probe). The embodiments of the steerable instrument and portions thereof are described in terms of their positon/orientation in a three-dimensional space. As used herein, the term "position" refers to the location of an object or a portion of an object in the three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" refers to the position of an object or a portion of an object in at least one degree of translational freedom and to the orientation of that object or portion of object in at least one degree of rotational freedom (up to a total six degrees of freedom); the term "shape" refers to a set of posture, positions, and/or orientations measured along the elongated body of the object. As it is known in the field of medical devices, the terms "proximal" and "distal" are used with reference to the manipulation of an end of an instrument extending from the user to a surgical or diagnostic site. In this regard, the term "proximal" refers to the portion of the instrument closer to the user, and the term "distal" refers to the portion of the instrument further away from the user and closer to a surgical or diagnostic site.

As used herein the term "catheter" generally refers to a flexible and thin tubular instrument made of medical grade material designed to be inserted through a narrow opening into a bodily lumen (e.g., a vessel) to perform a broad range of medical functions. The more specific term "optical catheter" refers to a medical instrument comprising an elongated bundle of one or more flexible light conducting fibers disposed inside a protective sheath made of medical grade material and having an optical imaging function. A particular example of an optical catheter is fiber optic catheter which comprises a sheath, a coil, a protector and an optical probe. In some applications a catheter may include a "guide catheter" which functions similarly to a sheath.

As used herein the term "endoscope" refers to a rigid or flexible medical instrument which uses light guided by an optical probe to look inside a body cavity or organ. A medical procedure, in which an endoscope is inserted through a natural opening, is called an endoscopy. Specialized endoscopes are generally named for how or where the endoscope is intended to be used, such as the bronchoscope (mouth), sigmoidoscope (rectum), cystoscope (bladder), nephroscope (kidney), bronchoscope (bronchi), laryngoscope (larynx), otoscope (ear), arthroscope (joint), laparoscope (abdomen), and gastrointestinal endoscopes.

In the present disclosure, when applicable, the terms "optical fiber", "fiber optic", or simply "fiber" refers to an elongated, flexible, light conducting conduit capable of conducting light from one end to another end due to the effect known as total internal reflection. The terms "light guiding component" or "waveguide" may also refer to, or may have the functionality of, an optical fiber. The term "fiber" may refer to one or more light conducting fibers. An optical fiber has a generally transparent, homogeneous core, through which the light is guided, and the core is surrounded by a homogenous cladding. The refraction index of the core is larger than the refraction index of the cladding. Depending on design choice some fibers can have multiple claddings surrounding the core.

Specific embodiments of the present disclosure are directed to improved robotically controllable endoscopes or catheters for application in minimally invasive surgery (MIS) procedures. MIS procedures involve the use of long rigid or flexible surgical instruments that are inserted into the body of a patient through small incisions or natural orifices. Today, there is wide range of well known endoscopic procedures. An important aspect of MIS endoscopy is the ability to "see" inside the body of the patient by directly inserting an imaging device into the area of interest. As the imaging device, most endoscopes use a high-resolution camera and a light source at the endoscope tip. The endoscope tip can be actively steered either manually by two thumb-controlled dials, or by a robotic actuator at the proximal end. Insertion and retraction of the endoscope into the patient body can also be performed either manually or robotically. Throughout this disclosure, working principles and novel improvements for robotic controlled endoscopic devices are described in detail. The application of such endoscopic devices includes procedures for both diagnostic and therapeutic purposes.

<Configuration and Operation of a Steerable Medical Instrument>

A general configuration and operation principles of steerable instrument 100 controlled by a robot system moo is described with respect to FIGS. 1A, 1B, 2A and 2B. As used herein, the steerable instrument 100 refers to a steerable catheter or endoscope having at least one steerable section which is manipulated by a mechanism which may be driven manually by operators or robotically by actuators. The robot system moo can include a continuum or multi-segment robot configured to take continuously curved geometries to move the endoscope probe or catheter longitudinally along tortuous paths. An example of a continuum robot is a snake-like endoscopic device, as described and presently embodied in applicant's previous patent or patent application publications including U.S. Pat. No. 9,144,370, patent publications US 2015/0088161; US 2018/0192854; US 2018/0243900; US 2018/0311006; US 2019/0015978; and US 2019/0105468, as well as in international publications WO2018204202; WO/2020/086749; WO/2020/092096; and WO/2020/092097, each of which are hereby incorporated by reference in their entirety for all purposes.

FIG. 1A illustrates a general structure of a continuum robot system 1000, according to one embodiment of the present disclosure. The system 1000 includes a computer system 400 (e.g. a system console), a robotic control system 300, and a steerable instrument 100 which is connected to the control system 300 via a handle 200. The steerable instrument 100 has a generally tubular shape with a proximal non-steerable section 102 and a distal steerable section 103 arranged along a central longitudinal axis Ax. The distal steerable section 103 includes a plurality of bending segments (1, 2, 3 . . . N); and at least one of these bending segments can be mechanically actuated by one or more control wires to bend the steerable instrument 100 at an angle β with respect to the longitudinal axis.

The steerable instrument 100 is a medial-grade steerable shaft having dimensions appropriate to reach a patient's organ depending on the specific application. The steerable and non-steerable sections of instrument 100 form an elongated tubular body coupled to, and controlled with/by, the handle 200. Expressed in the X-Y-Z Cartesian coordinate system, the tubular body of the steerable instrument 100 has a tubular cross section in an X-Y plane, and the longitudinal axis Ax along the Z-axis perpendicular to the X-Y plane. In other words, the distal end of the steerable instrument 100 points towards the Z-direction, and is configured and dimensioned for insertion into a patient's body part either through a small surgical incision or a natural orifice.

The control system 300 generally includes a controller 320 and an actuator system 310. The controller 320 may include a proportional-integral-derivative (PID) controller or other digital signal processor (DSP) along with suitable software, firmware and peripheral hardware, as it is known to persons having ordinary skill in the art. PID or DSP-based controllers are generally dedicated integrated circuits; however DSP functionality can also be implemented by other circuits, for example, by using field-programmable gate array chips (FPGAs). Therefore, in some embodiments, the control system 300 can be connected to a computer system 400 via a network connection 425. The controller or computer system 400, along with suitable software, firmware and peripheral hardware, operated by a microprocessor or central processing unit (CPU) 410 controls the functions of the continuum robot system 1000, as described in the remainder of this disclosure. Among other functions, the computer system 400 can provide a surgeon or other user with an image display device 420, such as an LCD or OLED, configured as a monitor screen 422 configured to display images and a graphical user interface (GUI) with a touchscreen to interact and remotely operate the steerable instrument 100. Alternatively or in addition thereto, the control system 300 and/or handle 200 can be connected to a handheld controller, such as a gamepad controller or a portable controller device like a smartphone or tablet (not shown).

The actuator system 310 includes a plurality of actuators or actuating motors (Motor 1 through M) equal to a plurality of control wires 110 (also referred to as drive wires) necessary for actuating and steering the instrument 100. The robotic control system 300 also includes and/or controls one or more sensors 304. Sensors 304 can include a strain sensor and/or a position sensor for each control wire 110. These sensors 304 serve to detect and/or measure compressive and/or tensile forces applied by the actuators to drive each control wire 110. The sensors 304 also output a signal 305 corresponding to the amount of compressive and/or tensile force (an amount of strain) being applied to a control wire 110. The sensors 304 could also output a signal 305 corresponding to an amount of movement (a distance) of displacement for each actuated control wire no, at any given point in time during a procedure. The output signals 305 from the sensors 304 (strain sensor and/or position sensor) for each control wire 110 are fed back to the controller 320 to control each actuator and control wire 110 individually with a feedback control loop. In this manner, each control wire 110 can be actively controlled to implement appropriate shaft guidance for navigating the instrument 100 through intraluminal paths of a patient's anatomy. During catheter navigation, the system continuously monitors the contact force that is exerted by the catheter tip by using a specially designed algorithm (e.g., as described in US 2007/0135803) and the sensors 304. If the contact force exceeds a preset limit, the system provides a warning, and catheter advancement is interrupted and the navigation path is corrected.

The handle 200 includes mechanical, electronic, electrical, and optical components which serve to provide electromechanical interconnection between the steerable instrument 100 and the control system 300. For example, the handle 200 may provide mechanical, electrical, and/or optical connections, and a data/digital acquisition (DAQ) system for interfacing the steerable instrument 100 with the control system 300. The handle 200 may also provide an access port 250, one or more mechanical dials or knobs 252, and a user interface 254. The one or more control wheels or knobs 252 are used to manually bend individual segments of the steerable section 103 in one or more directions. The access port 250 is used for insertion and extraction of tools into the tool channel 105, such as small forceps, needles, or electrocautery instruments and the like. The handle 200 is attachable to a robotic support platform 600 (e.g., a linear stage 601) to move the steerable instrument 100 in a linear direction L. The controller system 300 sends control signals to the support platform 600 and/or linear stage 601 via the handle 200 or/or an additional connection 205 such as a cable bundle.

As part of the user interface 254, the handle 200 may include one or more than one light emitting diode (LED) for providing operational status of the robotic steerable instrument 100 to a user. In an embodiment, the LED may include, for example, different light colors for respectively indicating normal operations (green light) and abnormal operations (red light). Alternatively, the LED may include blinking codes, for example, to indicate a type of abnormal operation. In addition, the user interface 254 may include an emergency on/off switch to manually stop actuation of the steerable instrument 100, in the event of an emergency.

Figure 1B:
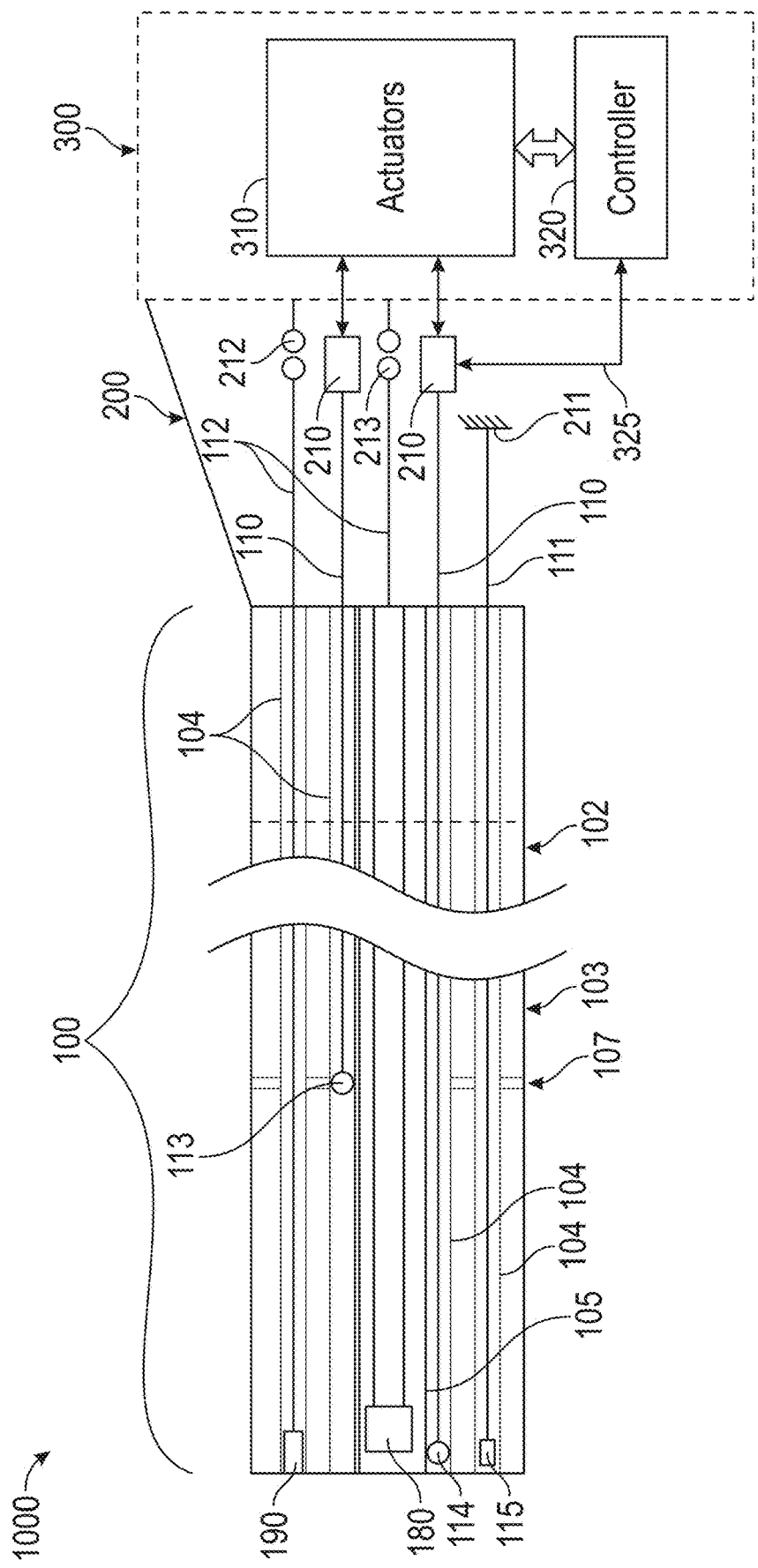
FIG. 1B illustrates in more detail the steerable instrument 100 having an elongate flexible sheath (elongate tubular body) with at least one tool channel 105 and a plurality of wire conduits 104 extending along the length of the sheath.

FIG. 1B illustrates in more detail relevant parts of the steerable instrument 100. The steerable instrument 100 has an elongate tubular shaft (elongate body) also referred to as a sleeve or sheath guide. Along the shaft's length, there are one or more working channels 105 extending along (typically inside) the tubular shaft, and a plurality of wire conduits 104 extending along (typically within) the wall of the tubular shaft. The one or more tool channels 105 will be refereed to as a "tool channel" for simplicity. The tool channel allows access for the tools (end effectors) to be delivered from an access port 250 to the distal end of the steerable section 103. The one or more channels 105 may also be used for sending or retrieving liquid or gaseous substances (e.g., air or water) to a target area, or for passing optical fibers and/or electric wires. Furthermore, the one or more channels 105 may be used for inserting one or more of a medical imaging device 180, such as an endoscope camera or a fiber-based imagining probe. An example of an endoscope camera includes, but is not limited to, a chip-on-tip (COT) camera, such as a camera with a miniature CMOS sensor and an illuminator arranged at the tip of the endoscope. Examples of fiber-based imaging probes include, but are not limited to, a near infrared auto-fluorescence (NIRAF) imaging probe, a spectrally encoded endoscopy (SEE) probe, an intravascular ultrasound (IVUS) probe, or an optical coherence tomography (OCT) imaging probe.

The steerable instrument 100 is configured to provide flexible access to intraluminal target areas with one or more than one bending curves to reach an intended target area usually located near (at a working distance from) the distal end of the instrument. Desirably, the steerable instrument 100 is capable of retaining torsional and longitudinal rigidity so that a user can control end effectors and/or imaging devices located at the distal end of the steerable section by remotely maneuvering the distal end of instrument 100 from the control knobs 252, the control system 300 and/or computer system 400. In order to provide such steerable functionality, the steerable instrument 100 is actuated with a plurality of control wires 110 which are arranged inside the wire conduits 104 along (typically within) the wall of the tubular shaft. Some of the control wires 110 are anchored at the distal end of the tubular shaft using wire anchors 114, and other control wires 110 can be anchored at certain predetermined distances from the distal end using wire anchors 113. In some embodiments, the steerable instrument 100 may include one or more support wires 111 (tendon wires). Support or tendon wires 111 can be optional at some locations of the steerable section, and are typically anchored at the distal end of the shaft with wire anchors 115, and can be mechanically grounded (attached) and/or biased to a support section 211 (e.g., the chassis, a mechanical spring, etc.,) of the endoscope handle 200.

In one exemplary embodiment, the steerable instrument 100 with six control wires 110 may have two pairs of control wires 110 (i.e., four control wires) anchored by wire anchors 113 in the midsection of the shaft (e.g., at one or more inflection points 107), and another pair of control wires 110 (two control wires) could be anchored by wire anchors 114 at the distal end of the shaft. In this manner, the steerable instrument 100 can have at least two (i.e., two or more) steerable sections controlled by 3 pairs of antagonistic control wires 110, where each wire extends through a separate wire conduit 104. According to one embodiment, the steerable instrument 100 has 3 locations with anchored control wires 110, and two locations with anchored support wires 111. The most distal anchor point has 3 control wires 110 and 3 support wires 111. The "middle" anchor point has 3 control wires and no support wires. And the proximal anchor point has 3 control wires and 3 support wires.

The wire conduits 104 allow anchorage and/or passage of control wires 110 used for steering (bending or twisting) at least one segment or section of the shaft. In addition, at least some wire conduits 104 can be used to pass one or more electrical cables 112. Electrical cables 112 are configured to establish an electrical connection between an electronic device arranged at the distal end or within the steerable section 103 and a terminal (212 or 213) or a signal processing circuit located outside of the proximal end of the instrument. For example, an electrical cable 112 can be used to connect one or more electromagnetic (EM) sensors 190 to first electrical terminals 212 located at the handle 200. In some embodiments, the wire conduits 104 can also be used to pass additional electrical cables 112 which can connect the imaging device 180 (a camera) to second electrical terminals 213 also located at the handle 200.

As used herein, an electrical cable 112 refers to a conductive cable or cable bundle including one or more wires configured to conduct an electrical signal (analog or digital) for connection of an electronic component, such an EM sensor or an endoscope camera (videoscope) located in or at the distal end of the catheter body, to signal processing circuitry located outside of the catheter body. An electrical cable 112 may be formed from one or more strands of an electrically conductive metal, such as silver, plated copper, copper, silver, gold, aluminum, and alloys thereof. The electrical cable 112 may be covered by a conventional electrically insulating material (jacket), such as polyurethane, polyester, nylon, and the like. An overall diameter of the electrical cable may be in a range of about 0.002 to 0.050 inches, or in a range of about 0.002 to 0.030 inches. These are merely examples of possible dimensions to illustrate the delicate nature of electrical cables 112 which are incorporated into steerable instrument 100. Since all aspects of these instruments continue to be miniaturized, it is expected that electrical cables 112 will also become smaller (thinner) and more delicate. Therefore, while an electrical cable measuring around 0.006 inch in diameter may be used, the cable may not have a round or circular cross section, but it may be more like oval cross section. For example, the electrical cable 112 could measure about 0.002×0.010 inches in cross sectional dimensions whether oval or rectangular. Therefore, a unique cable configuration that may have a non-round (non-circular) cross section may be advantageous in some situations. Moreover, depending on the specific application, the electrical cable 112 can be a coaxial cable, a twisted multi-cable bundle, or an irregularly wound or reinforced cable which is configured to satisfy the parameters and Young's modulus stipulated in Table 1 described later.

At the proximal end of the instrument 100, the handle 200 is configured to provide a mechanical linkage and an electromechanical interface between the steerable instrument 100 and the control system 300. In one embodiment, the handle 200 provides a plurality of electromechanical connections 210 (one connection for each of the control wires 110) so that an actuator system 310 can mechanically actuate each control wire 110. Each electromechanical connection 210 is in operative connection with the one or more sensors 304 to create a feedback loop 325 (based on signal 305) for controller 320. The controller 320 is used to electronically control the operation (movement) of each control wire 110 based on one or more of tensional, compressive, and/or torsional forces applied to each control wire 110.

Figure 2A:
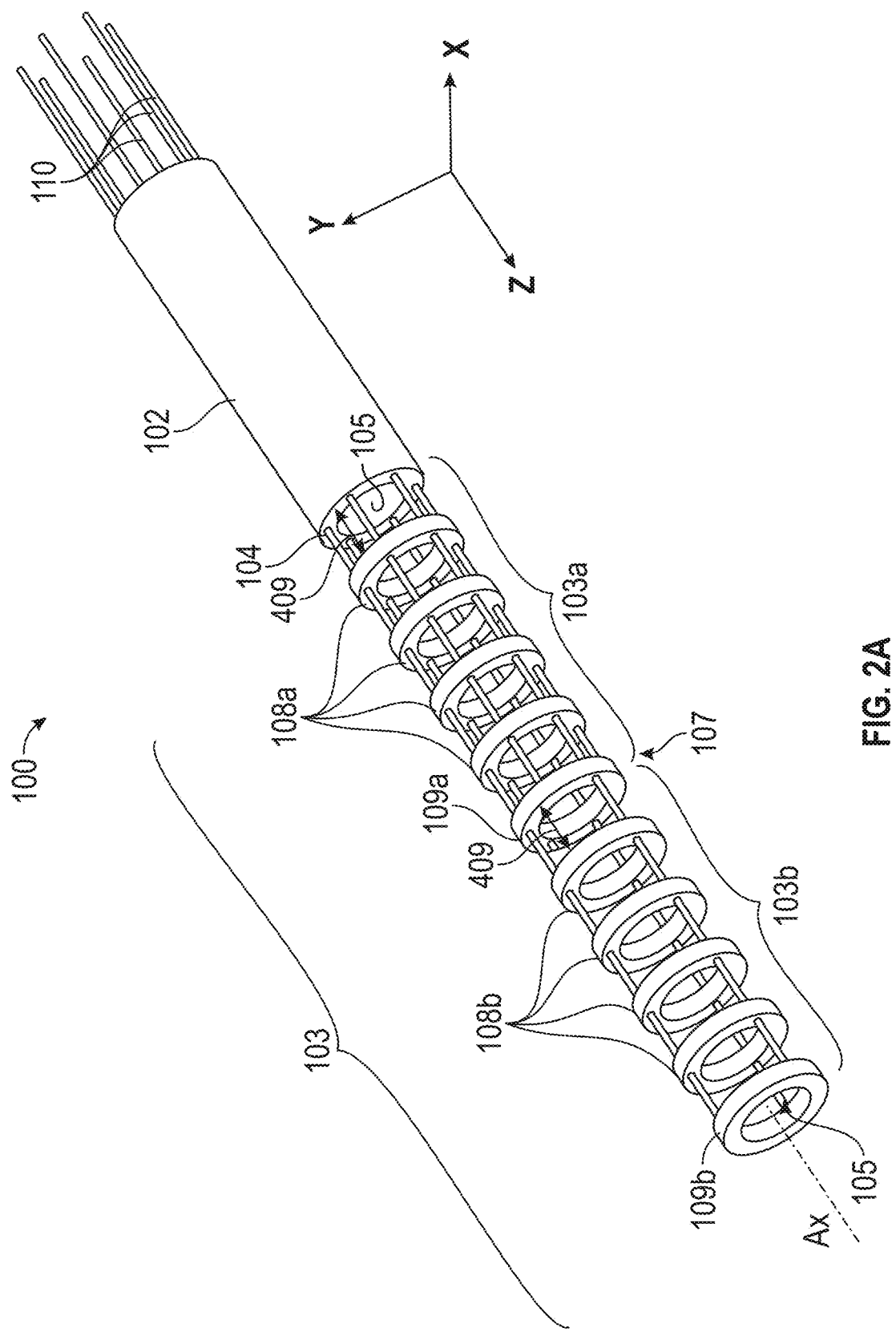
FIG. 2A is a perspective view of an exemplary steerable instrument 100 having a non-steerable section 102 and a steerable section 103, in a non-bent state.
Figure 2B:
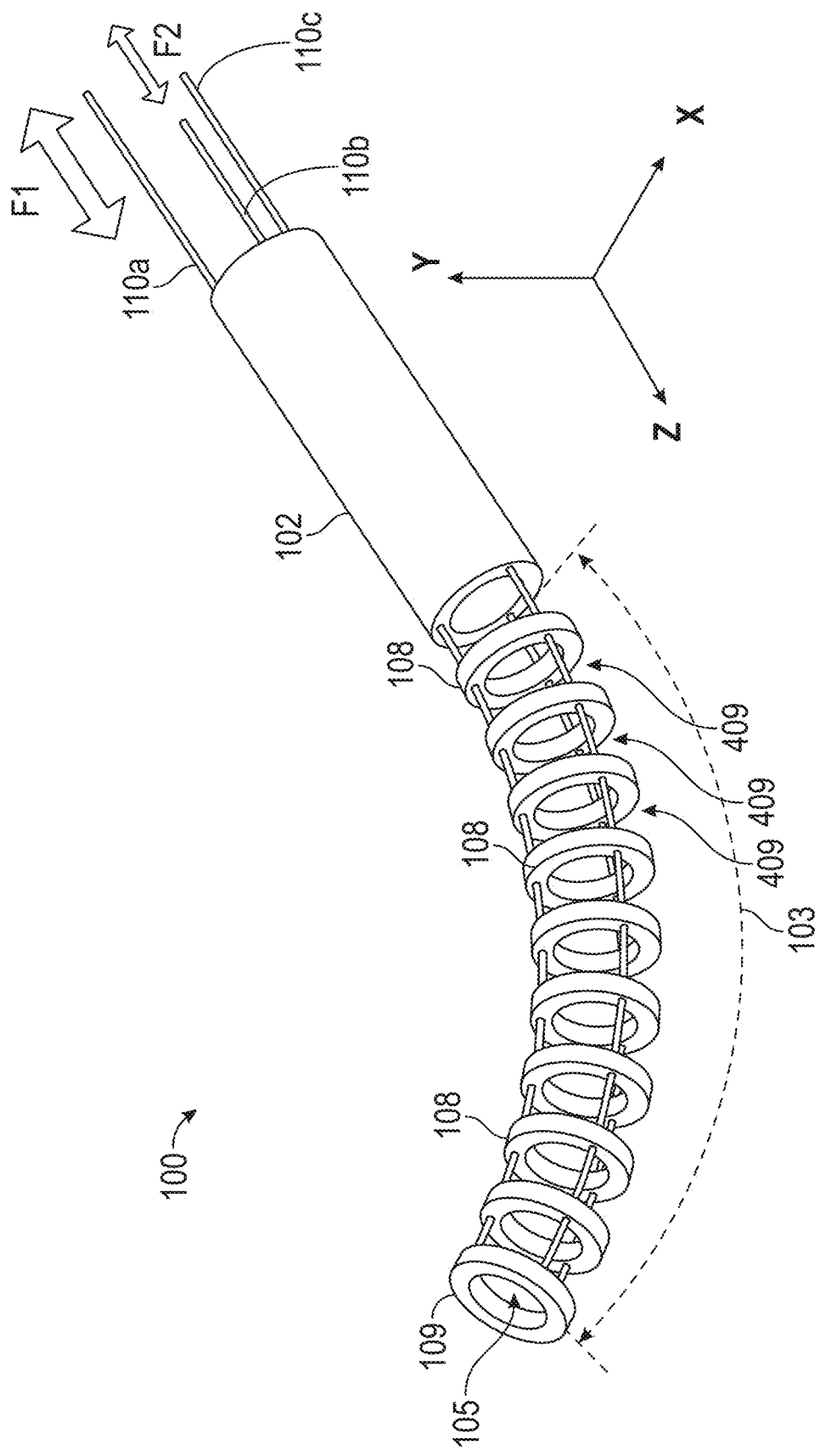
FIG. 2B shows an example of bending or steering a single segment of steerable section 103 of steerable instrument 100.

FIG. 2A and FIG. 2B each shows a perspective view of the steerable instrument 100 in a non-bended and bended state, respectively. The proximal non-steerable section 102 is a tubular (hollow) shaft with a central lumen which serves a tool channel 105 and a plurality of wire conduits 104 within the wall of the tubular shaft. The non-steerable section 102 of the steerable instrument has a hollow cylindrical shape with the longitudinal axis Ax extending along the Z-axis direction and a plurality of conduits or through holes extending within the wall of the cylindrical shape. In the non-bended state, the wire conduits 104 are preferably substantially equidistant, symmetrically arranged, and parallel to the longitudinal axis Ax. The steerable section 103 is divided into a plurality of bending segments 103a-103b joined at an inflection point 107 by a wire-anchor member 109a. Each bending segment of steerable section 103 includes a plurality of wire-guide members 108 (wire-guiding members or rings), and a wire-anchor member 109 (anchor member). Wire-guide members and wire-anchor members have the same shape and structure, but different function. In addition, some of the anchor members also act as wire-guiding members (or wire guides). For example, wire-anchor member 109a has control wires anchored to it and control wires passing through it non-anchored. A wire-anchor member 109b has control wires anchored to it, and it may also have support wires and/or an EM sensor attached to it.

In FIG. 2A, a first bending segment 103a includes four wire-guide members 108a and one wire-anchor member 109a. A second bending segment 103b includes four wire-guide members 108b and one wire-anchor member 109b. The wire-guiding members are arranged at predetermined distances from each other so as to form a plurality of void regions 409 along the steerable section 103. A plurality of control wires 110 extend from the proximal end to the distal end of the steerable instrument 100. The control wires 110 are initially passed through wire conduits 104 formed along (within) the wall of non-steerable section 102, and then routed through holes in the plurality of wire-guide members 108 and wire-anchor members 109. The anchor members 109a, 109b and guide members 108a, 108b have an annular shape (disk or ring shape) with the center axis thereof extending along the Z-axis direction, and the inner and outer diameter orthogonal to the axis direction. In the wire-guiding members, the wire conduits 104 (wire lumens) are through holes parallel to the axis direction formed around the surface of each disk. Here, those skilled in the art will understand that the proximal section 102 and wire-guiding members and wire-anchor members of distal section 103 are not limited to cylindrical-, disk- or ring-shaped structures. As long as the functionality of the steerable instrument 100 is met, the catheter body substructures can have any geometrical shape. For example, instead of disk, ring or cylindrical-shaped surfaces, at least one surface (e.g., the inner surface or outer surface or both) of the tubular shaft can have a hexagonal, octagonal, or similar polygonal shapes, with an overall dimension that fits within an inner diameter (ID) or outer diameter (OD) specified herein.

In FIG. 2A, among the plurality of control wires 110, some control wires pass through wire conduits 104 from the proximal end of the steerable instrument 100 (catheter body) to the first anchor member 109a, and some control wires 110 advance from the proximal end to the second anchor member 109b. The control wires 110 are fixedly attached to the anchor members, for example, by bonding, pinning, ultrasonic or heat or laser welding, pressure fitting, or attached by screws. All control wires 110 are coupled, at the proximal end thereof, to individual motors or actuators (i.e., to an actuator system 310, as shown in FIG. 1B).

The non-steerable section 102 has a function of transmitting an actuating force from the actuator system 310 to the bending segments of the steerable section 103 substantially without slack. To that end, the control wires 110 passing through the wire conduits 104 are driven in a linear push or pull direction L (parallel to the Z-axis direction), preferably without any buckling or slack. The control wires 110 can be metal wires, for example, plano-type wires, stainless-steel wires, nickel-titanium-alloy (nitinol) wires, or shape-memory-alloy (SMA) wires configured to push or pull a segment of the steerable section 103 according to an actuating force (tensile or compressive force) provided by one or more actuators of the control system 300. On the other hand, support wires 111 are non-actuated wires, but are configured to restore the steerable instrument to its passive position.

The steering motion (bending or twisting) of the steerable instrument 100 is explained next. For simplicity, the actuating of a single bending segment of the steerable section 103 is explained with reference to FIG. 2B. In the case of FIG. 2B, an exemplary steerable instrument too includes, from the distal end to the proximal end thereof, the steerable section 103 made of single bending segment and the non-steerable section 102 made of a tubular shaft with a central opening therein. A plurality of control wires 110a, 110b, and 110c extend from the proximal end to the distal end of the steerable instrument too along wire conduits 104 formed in (within) the wall of the non-steerable section 102 and through wire conduits 104 through holes) of guide members 108. One or more of the control wires 110 are fixedly coupled, at the distal end of the shaft, to an anchor member 109. The control wires 110 are also coupled, at the proximal end of the shaft, to individual actuators or motors of the actuator system 310. In this manner, the control wires 110 are selectively actuated by sliding with respect to the guide members 108 by the action of an actuator or motor connected at the proximal end of each control wire (refer to FIG. 1A-1B). One of the three control wires 110 (e.g., control wire nob in FIG. 2B) can fixed (or mechanically grounded) with respect to all guide members 108, and the remaining two control wires 110 (e.g., control wires 110a and 110c) are slideable with respect to the guide holes of the guide members 108.

In bending the steerable instrument 100, each control wire 110 is individually controlled by a respective actuator or motor. For example, in FIG. 2B, while control wire 110b may be fixed or anchored to anchor member 109, control wire 110a is pulled with a first control force $F_1$, and control wired 110c is pulled with a second control force $F_2$ different from force $F_1$ (control force $F_2$ is smaller than control force $F_1$, in this example). In this manner, the bending segment 103 can be actuated and bent in a desirable direction (direction of force $F_1$), in accordance with a combination of the driving amounts (strain) or linear displacements of control wires 110a and 110c. To control the posture of the distal end of the steerable instrument too, driving two (or at least one) of the plurality of control wires 110 would be sufficient. As the forces $F_1$ and $F_2$ are applied to the control wires 110a and 110c, respectively, a corresponding sensor 304 detects the tensile force applied thereto. Here, it should be noted that forces $F_1$ and $F_2$ are not limited to tensile forces exerted by pulling the control wires 110. Forces $F_1$ and $F_2$ can also be compressive forces applied to the control wires 110 by mechanically pushing the control wires by a desired amount of compressive force.

While the case of driving the control wires 110 anchored at the distal end of a single bending section 103 has been described above with respect to FIG. 2B, if control wires of all bending sections of FIG. 2A are driven, the postures of each bending section 103a and 103b can be independently and selectively actuated to bend or twist the steerable section 102 and thereby produce a snake-like movement, depending of the driving amounts of the individual control wires driven by actuators of the actuator system 310 (drive unit). Further, a mechanism that twists or rotates the wire-driven steerable instrument 100 about its longitudinal axis may be additionally provided. In order to provide a certain amount of rotation or twisting action to the steerable instrument 100, a bending section may be first bent in a desirable direction by driving only one control wire 110, and then rotating the entire shaft by actuating a second control wire 110 in a different bending section. Such manipulation of the steerable instrument 100 can be implemented based on well known mechanical and kinematic principles, for example, as described in U.S. Pat. No. 9,144,370 which is hereby incorporated by reference herein for all purposes.

According to one embodiment, the steerable instrument 100 shown in FIG. 2A-2B may have an outer diameter of about 0.14 inches, with a distal steerable section being around 2.0 inches in length, and the total length of the instrument 100 being about 24 inches. The anchor members 109 have wire conduits 104 and a tool channel 105 similar to the wire-guide members 108; both are typically constructed from medical-grade plastics or similar composites. These materials allow for fabrication of flexible, yet torsionally resilient steerable instruments, such as catheters and endoscopes of reduced dimensions. For example, other prototype dimensions for a steerable instrument 100 are about 3.3 mm outer diameter (OD), 2.4 mm inner diameter (tool channel), and about 550 mm of total length. These exemplary dimensions are given for the purpose of illustrating sizes and dimensions of steerable instruments disclosed according to the present disclosure. However, a person of ordinary skill in the art will understand that actual dimensions will depend on the specific application of the steerable instrument 100.

Next, robotic and/or manual navigation of the steerable instrument 100 is explained. In general, either during insertion or retraction of the steerable instrument 100 through a patient's anatomy, the center line of the lumen (e.g., an airway) is the desired trajectory to be followed during active control of the bending segments of the steerable section 103. To that end, known guiding techniques of steerable instruments, such as robotic guided catheters or endoscopes, can be used. In general, various known concepts of shaft guidance control the steerable instrument with the goal of forcing the flexible shaft to keep to a desired trajectory. In one such example, when using a shaft guidance system, the steerable instrument is advanced through a lumen while sensors measure the insertion depth of the shaft-guide and the angulations of user-controlled steerable tip segments to obtain trajectory information. The trajectory information is stored in a memory of the system and continuously updated. After a short advance in insertion depth, the shape of the steerable shaft-guide is corrected by adjusting (rotating, twisting, or bending) segments of the instrument in such a way that the new shape closely matches the desired trajectory. This process is repeated until a target area is reached. The same process is applied when the steerable instrument is withdrawn from the patient. See, e.g., US 2007/0135803, which is incorporated by reference herein for all purposes. In some instances, it is also possible to initially manually advance the steerable instrument through a lumen, and then preform robotic control thereafter. In either case, when the steerable instrument 100 travels through a lumen, the bending of the steerable section 103 causes tension and strain on the electrical cable 112.

<Strain of Electrical Cable>

Figure 3A:
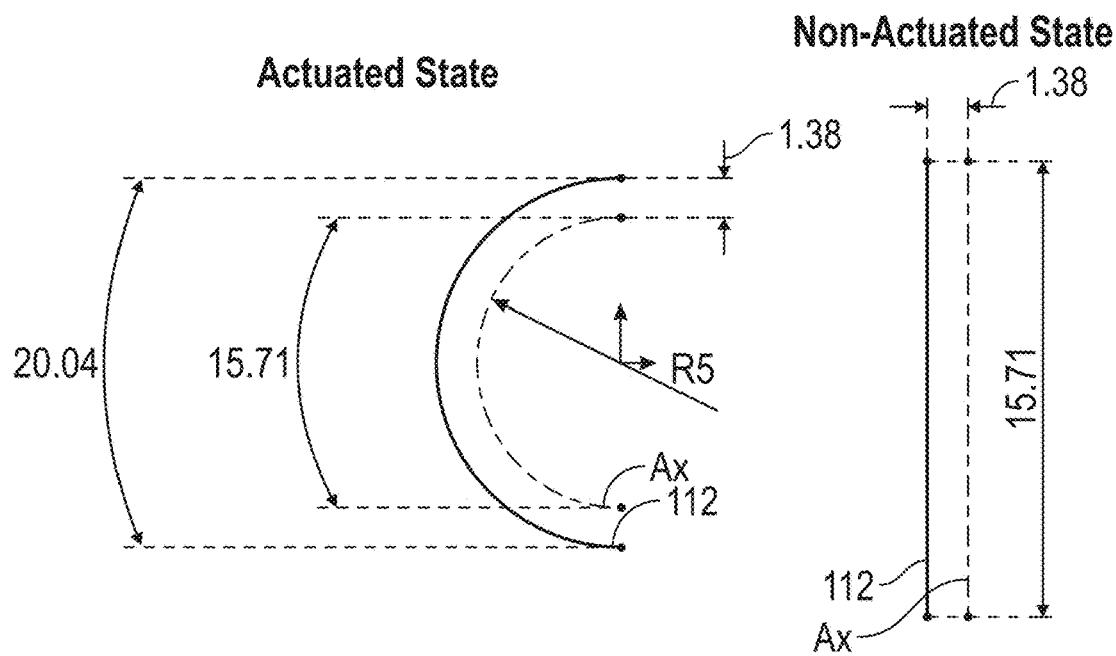
FIG. 3A illustrates an example of strain condition exerted on the steerable section 103 located at the distal end of the steerable instrument 100.
Figure 3B:
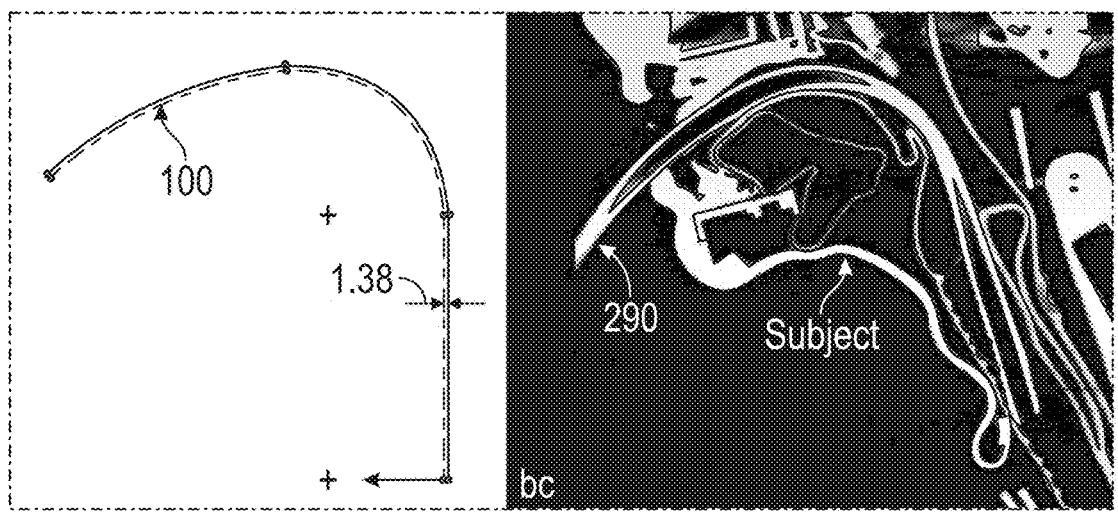
FIG. 3B illustrates an example of strain condition exerted on the non-steerable section 102 located at the proximal end of the steerable instrument 100.
Figure 3C:
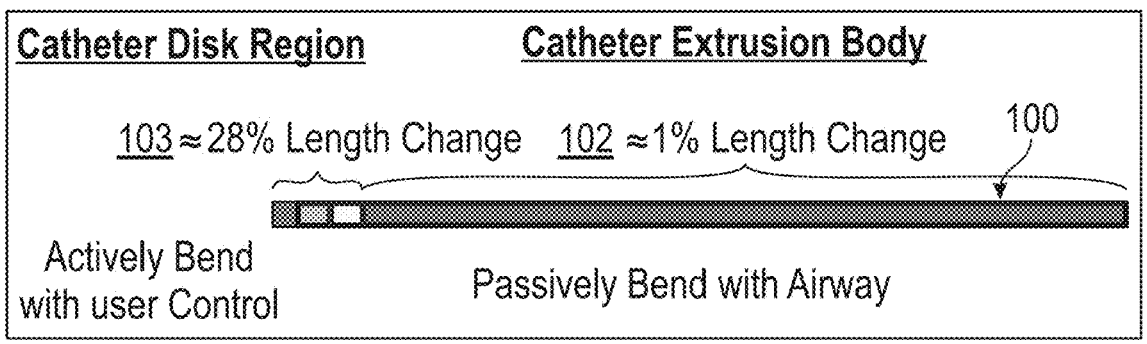
FIG. 3C illustrates exemplary length change parameters for electrical cable 112 under strain conditions of the steerable instrument 100.

More specifically, as mentioned above, when the steerable instrument 100 (e.g., a catheter or endoscope) takes on a curved geometry during the steering operation, the length of electrical cables 112 becomes longer than the straight (original) wire length because the electrical cable must adapt to the curved geometry taken by the steerable instrument. This creates a strain condition on the electrical cable which in turn negatively impacts the maneuverability of the steerable instrument. FIGS. 3A, 3B, and 3C illustrate the parameters considered when an electrical cable 112 undergoes a strain condition when at least one of the bending segments of the steerable instrument 100 is actuated.

Here, it should be noted that there are two distinct "regions" or sections where the disclosed cable strain relief design applies to the steerable instrument 100. First, the non-steerable section 102 is a catheter body region located proximally, and the steerable section 103 is a catheter disk region located distally, from the endoscope handle 200. Each region has a unique set of design requirements, and thus each region incorporates different design elements, according to the "strain relief" parameters defined by the present disclosure.

FIG. 3A illustrates a strain condition for the steerable section 103 (the catheter disk region) when the catheter central axis is bent to a 5 millimeter (mm) radius of curvature, which results in a cable length change of approximately 28% due to the strain condition. More specifically, as shown in FIG. 3A, a straight portion of electrical cable 112 initially lays parallel to the instrument axis Ax, in a non-actuated state. However, when at least one portion (the steerable section 103) of the instrument 100 is bent and takes a curved geometry, the electrical cable 112 undergoes a strain condition which causes the cable to become longer. For example, the left-hand side of FIG. 3A shows the electrical cable 112 is bent with a radius R5 to take the same curved geometry to accommodate to the bended shape of the distal portion of the steerable instrument 100. In this case, since the electrical cable 112 is offset from the instrument axis Ax, the bending creates a strain condition on the electrical cable 112. As the example shown on the left-hand side of FIG. 3A, for a 15.71 mm piece of straight electrical cable 112, which is offset from the longitudinal axis Ax by about 1.38 mm, when bent with a curvature R of 5 mm radius, the electrical cable 112 undergoes an approximately 28% length change due to the strain condition. The change in length (≈4.30 mm) of the cable 112 is calculated by comparing the initial straight length (15.71 mm) to the bent final length (20.04 mm).

FIG. 3B illustrates an example of strain conditions for the steerable instrument 100 under a simulated robotically assisted intubation procedure. Under such procedure, the catheter body undergoes a length change of approximately 1.2% for the straight non-steerable section 102 (catheter extrusion body region) of the steerable instrument 100 under nominal strain conditions. Namely, the nominal strain condition is caused by manipulation of the instrument 100, but without actively bending the non-steerable section 102. This nominal condition was calculated via magnetic resonance imaging (MRI) phantom experimental data collected by the inventor under laboratory conditions. The left-hand side of FIG. 3B is a SolidWorks® image, which represents a shape of the steerable instrument 100 during a procedure. The right-hand side of FIG. 3B is an MRI image of an ET (endotracheal) tube 290 inserted into a subject or patient. In an intubation procedure, the steerable instrument 100 is first guided through the ET tube without actively bending steerable section 103, but the proximal section still experiences nominal strain conditions. Extrapolating the 1.2% calculated strain to the length of the non-steerable section 102 of the catheter body results in a length change of about 6.6 mm (550 mm×0.012). To accommodate these strain conditions of the electrical cable 112 both at the proximal non-steerable section 102 and at the distal steerable section 103 of the steerable instrument 100, the present disclosure considers the strain of the electrical cable separately in at least each of the two sections. In some embodiments, the strain of the electrical cable is considered separately in more than two sections, e.g., by anchoring the electrical cable along the wire lumen to isolate tension in one portion of the cable from another.

FIG. 3C is a graphical representation of the non-steerable section 102 and the steerable section 103 of the steerable instrument 100 with respective percentages of wire length change due to strain conditions in each section. The non-steerable section 102, which is typically made of extruded material, is the longest section of the catheter body. This section is rigidly connected to the catheter handle 200, and is normally not actively bent during operation. Under operation, the non-steerable section 102 becomes passively bent when the steerable instrument 100 is guided through the patient's anatomy (e.g., an airway) and through other guiding instruments, such as the ET tube 290 shown in FIG. 3B. More specifically, the catheter extrusion body section becomes nominally bent when the catheter touches a patient's anatomy (e.g., the inner wall of the patient's airway) and is guided through ET tube 290. On the other hand, steerable section 103 is made of a plurality of wire-guiding and wire-anchoring disks which are arranged distally to the section 102 in groups of steerable segments. As mentioned above, the steerable section 103 includes a plurality of bending segments; and these segments are actively bent with user control of the steerable control wires 110.

Therefore, during actuation of the steerable instrument 100, the present disclosure considers that there are at least two different "regions" of cable strain relief to be considered within the sections of the steerable instrument 100. The two regions are the extrusion body region (or non-steerable section 102) of the shaft located proximally to the handle 200, and the catheter disk region (or steerable section 103) located distally to the handle 200. Each region has a unique set of design requirements, and thus each region must incorporate different design elements. These two regions are intended to be isolated from each other in terms of strain relief, such that strain forces encountered by the electrical cable 112 in the proximal region of the instrument 100 do not transfer to the same electrical cable 112 in the distal region. Here, it is noted that having two or more portions of the electrical cable isolated is desirable for manufacturing considerations (e.g., by securing the electrical cable along at least one point of the extrusion body, the assembler would not be able to pull the "slack" from the distal region). From a device usage perspective, however, cable strain relief would still perform as intended even if these regions were in fluid communication with each other. In other words, although some embodiments describe physically isolating two or more sections of the electrical cable to mitigate transfer of strain therebetween, in other embodiments isolation is not a requirement for the strain relief to function properly.

<Strain Relief Elements Arranged in Void Regions of Steerable Section>

Figure 4A:
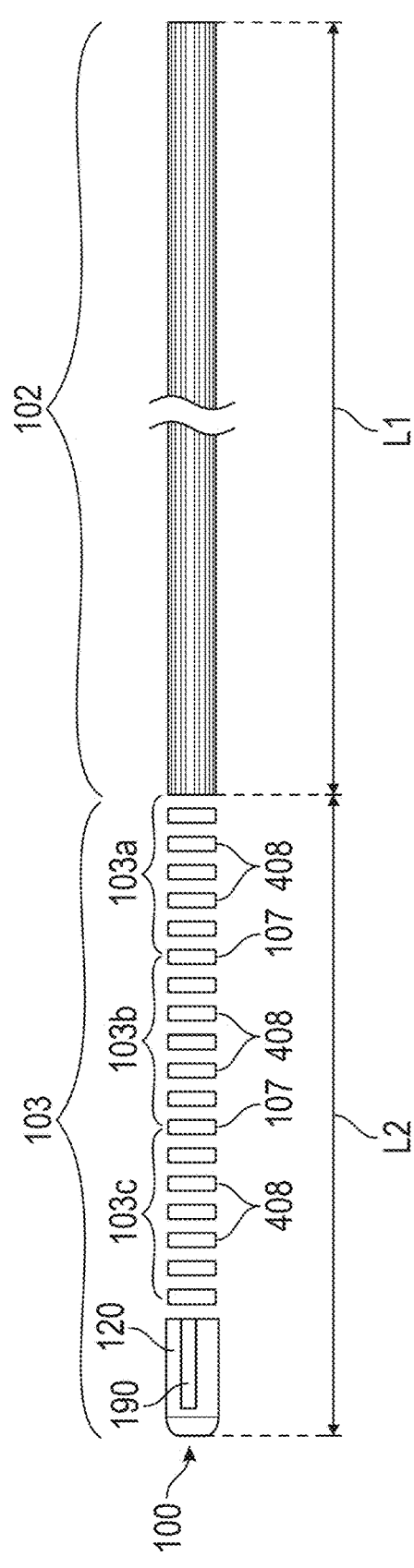
Figure 4A:
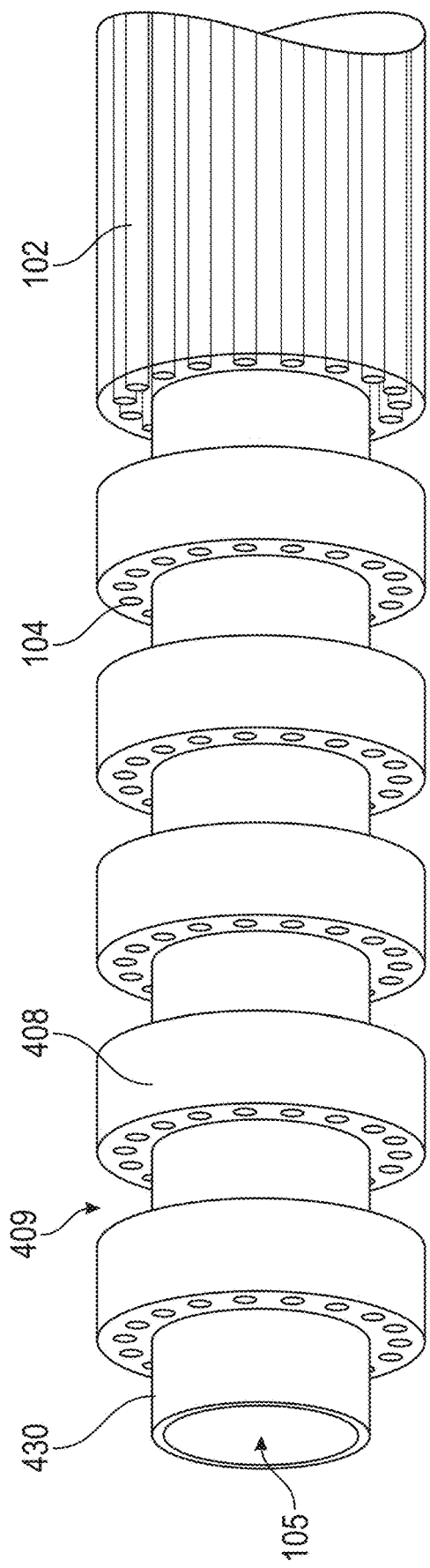

FIG. 4A, FIG. 4B1, FIG. 4B2, FIG. 4C, and FIG. 4D illustrate various details of a strain relief design for a portion of the electrical cable 112 arranged in the steerable section 103 of the steerable instrument 100. FIG. 4A illustrates the general structure of a simplified version of the steerable instrument 100. FIG. 4B1 shows the steerable instrument 100 formed as single component. FIG. 4B2 shows the electrical cable 112 anchored at the proximal section 102 and having strain relief portions arranged in void regions 409 of the steerable section 103. FIG. 4C and FIG. 4D respectively illustrate three-dimensional renderings of the steerable section 103 where the electrical cable 112 can be arranged in void regions 409 and routed either over the control wires 110 or under the control wires no.

As shown in FIG. 4A, the instrument 100 incudes the non-steerable section 102 (extrusion body region) having a length L1, and the steerable section 103 (disk region) having a length L2, in this order from the proximal to the distal end. The steerable section includes an atraumatic distal tip 120 which includes one or more sensors (EM sensor 190). In general, the length L1 is greater than the length L2. In one exemplary embodiment, the length L1 is about 550 millimeters (mm) and the length L2 is about 50 mm. In other words, according to one embodiment, the non-steerable section 102 can be approximately ii times longer than the steerable section 103. However, in general, the dimensions L1 and L2 can be adjusted according specific applications. In one embodiment of the steerable instrument 100, the length L2 of steerable section 103 can be increased to 75 mm while the length L2 remains at about 50 mm. In this case, there is a ratio of L1/L2=15. Therefore, it is envisioned that the ratio L1/L2 can be in range from about 10 to 20.

The non-steerable section 102 is made of solid extruded material with at least one tubular tool lumen or tool channel ion. The steerable section 103 includes a plurality of bending segments 103a, 103b, 103c, etc., and an atraumatic distal end or tip 120. Each of bending segments 103a-103c includes a plurality of wire-guiding members 408 (equivalent to wire-guide members 108 shown in FIGS. 2A and 2B). In the disk region or steerable section 103, the bending segments 103a-103c are formed by arranging, distally to the non-steerable section 102, a number of wire-guiding members 408 alternately with void regions 409. The bending segments are joined to each other at one or more inflection points 107, by a wire-anchoring member (109a in FIG. 2A), such that each bending segment can be independently actuated.

In some embodiments, the components of the steerable instrument 100 are described as separate components. In other embodiments, the catheter body or at least a portion thereof can be fabricated as a single component. FIG. 4B1 shows a perspective view of the steerable instrument 100 formed as a single component. According to FIG. 4B1, the wire-guiding members 408 (disk-shaped or ring-shaped members) and an inner sheath 430 can be fabricated as a single component to define therein a tool channel 105, wire-conduits 104, and void regions 409. For example, at the steerable section 103 and/or the non-steerable section 102 may start as a typical multi-lumen extrusion, and then laser micro-machined to create the void regions 409 and ring features. Alternatively, at the steerable section 103 and/or the non-steerable section 102 may fabricated as single component by additive manufacturing, also known as 3D printing.

FIG. 4B2 shows an example of the manner in which an electrical cable 112 can be arranged in the steerable section 103. In the steerable section 103, the ring-shaped wire-guiding members 408 are arranged at a predetermined distance or pitch P creating a plurality of void regions 409 alternated with the wire-guiding members 408. In this embodiment, the steerable section 103 incorporates strain relief features (unconstrained first portions of electrical wire 12sr) disposed between and potentially within the catheter disks and/or within other catheter substructures. Here, to form the strain relief elements, first, the electrical cable 112 is passed from the proximal end through wire conduits 104 along the wall of the non-steerable section 102. In other words, in the non-steerable section 102, at least one electrical cable 112 is passed through the shaft of the catheter body offset with respect to the longitudinal axis Ax. Then, at an anchor point 413, the electrical cable 112 is anchored (potentially selectively) to the catheter extrusion body allowing for isolation of cable strain forces encountered in the proximal section 102 from being transferred to the distal section 103. Here, portions the electrical cable 112 (second or constrained portions of the electrical cable) can be anchored at the distal end of the non-steerable proximal section 102, or at predetermined points along the length of the non-steerable section 102, and/or along predetermined points along the steerable section 103. Anchoring the electrical cable 112 to the extrusion body region can be done by, for example, pressure fitting, gluing, "reflowing" the catheter material around the cable, laser welding, "wrapping" or winding the cable around a portion or feature of the extrusion body, affixing the cable to an additional component that constrains movement within the wire conduit, or otherwise affixing the electrical cable 112 to the wall of the tubular shaft, such that the electrical cable does not substantially slide with respect to the body of the catheter. For example, bonding the cable to a "plug" that resides within a corresponding cutaway feature in the lumen. The plug then constrains the motion of the cable to a limited space.

After the electrical cable 112 is securely anchored to the non-steerable section 102, the electrical cable 112 is carefully passed through the wall of the wire-guiding members 408 and portions of the cable are loosely arranged in void regions 409 until the length of the cable is distributed along the length of the steerable section 103 and the distal end of the cable is then connected to one or more electronic components, such as the EM sensor 190. In each void region 409, a portion of the electrical cable 112 is loosely wrapped or coiled or folded to form a plurality of strain relief cable portions 12sr. Naturally, the electrical cable 120 can be assembled either first attaching either permanently or temporarily the sensor into the slot in tip 120 in FIG. 4A, wrapped around the distal end as shown in FIG. 4B, then inserted into the lumen in the proximal section 102. The electrical cable may or may not be attached at the anchoring point 413. In other words, assembling the electrical cable into the catheter body and forming strain relief portions 12sr could also be done in reverse order or in any arrangement of these steps or other steps.

FIG. 4C and FIG. 4D show perspective views (3D renderings) of the manner in which the electrical cable 112 can be arranged in void regions 419. Specifically, in FIG. 4C and FIG. 4D, the steerable section 103 includes, arranged coaxially with the tool channel 105, an inner sheath 430 and an outer sheath 450. The wire-guiding members 408 are arranged between the inner sheath 430 and the outer sheath 450, and the control wires 110 are passed through wire conduits 104. The wire conduits 104, and hence the control wires 110, are distributed substantially symmetrically around the circumference of each wire-guiding member 408. In the embodiment of FIG. 4C, each strain relief portion 12sr of the electrical cable 112 is arranged wrapped helicoidally over the control wires 110 so that the electrical cable is loosely contained substantially concentric with the tool channel 105 between the steering control wires 110 and the outer sheath 450. In the embodiment of FIG. 4D, each strain relief portion 12sr of the electrical cable 112 is arranged wrapped helicoidally under the control wires 110 so that the electrical cable is loosely contained substantially concentric with the tool channel 105 between the steering control wires 110 and the inner sheath 430. In either case, the strain relief portions 12sr of the electrical cable 112 are arranged substantially concentric, but non-orthogonal, to the longitudinal axis Ax.

More specifically, in order to provide a certain amount of slack for strain relief, the electrical cable 112 is revolved around the tool channel of the steerable instrument 100 and arranged to form one or more strain relief portions 12sr along the length of of each void region 409 in the steerable section 103. The electrical cable 112 may loop around the tool channel 105, over the control wires 110, to form at least a partial revolution or multiple revolutions in each void region 409. Alternatively, the electrical cable 112 may loop around the tool channel 105, under the control wires 110, to form at least a partial revolution or multiple revolutions. The strain relief portions 12sr may form in every void region 409 or in only selected void regions 409. The electrical cable 112 can be looped to form the strain relief portions coiled around the tool channel either less than one revolution (e.g., 45 degrees) or one full revolution (360 degrees) or more than one revolution (e.g., between one to two revolutions) or two full revolutions or more than two revolutions.

FIG. 4D also shows the wire-guiding members 408 (ring-shaped members) have a predetermined thickness T, and are arranged substantially at equal intervals or pitch distance P. As a result, in this embodiment, the void regions 409 are substantially the same size as the predetermined thickness (length) of the wire-guiding members 408. In one embodiment, the "void regions" 409 are designed with specific dimensions (e.g., 1 mm width at 1 mm intervals), which is important to the overall design of the steerable instrument. In general it is possible to define the relation between the longitudinal dimensions of each wire-guiding member 408 to space occupied by each void region 409 as a ratio. For example, a ratio T/P in a range of between 0.5 and 1 relates the disk length to the length of the void region (T/P) with the length measured along the Ax axis. In this regard, it must be considered that the specific dimensions of the void regions 409 and thickness of the wire-guiding members 408 enable minimal contact between the electrical cable 112 and other structures of the steerable instrument too. Therefore, in general, it is more advantageous to have more void length than ring length as this ratio enables a smaller bend radius of the distal section. Further, each void region 409 can be designed according to where the most strain relief is needed, and thus the strain relief portions 12sr may have the most movement within the void region 409 when the steerable instrument adopts a given geometry during actuation of the steerable section 103 for navigation through tortuous paths.

Here, in order to effectively mitigate strain conditions in the electrical cable 112, the friction between the electrical cable 112 and any other substructure of the steerable instrument too needs to be minimized. This is most notably true for delicate structures where friction levels even in fractions of a Newton can be meaningful. The reason for this is that, in delicate medical devices, friction leads to inhibited flexibility. For example, in steerable catheters or endoscopes of minimized diameter, as the force to bend the steerable instrument to a given geometry increases, even a slight friction of the electrical cables can hinder the normal operation of the instrument. Additionally, frictional forces beyond a predetermined strain (e.g., higher than 1.8 Newton) could result in damage or failure of the electrical cable itself. Also, friction of the electrical cable with the catheter substructures (e.g., the control wires and/or wire-guiding member) can cause a "pinch point" to develop in the electrical cable and can create a sharp bend during catheter use. This pinch point can eventually lead to an open circuit condition. Therefore, it is important to minimize contact between the electrical cable and the catheter body. However, due to the above-mentioned constraints, at least certain contact may be unavoidable.

Nevertheless, the present application provides various embodiments wherein the electrical cable includes strain relief elements arranged in one or more void regions such that when the electrical cable is subjected to a tensile load by the actuating force bending the distal section of the catheter body, the strain relief elements within the one or more void regions minimize the tensile load on the electrical cable. In particular, when the electrical cable 112 is wrapped around the body of the steerable instrument too but remains contained within the wall of the outer sheath 450, as shown in FIG. 4C, the strain relief portions 12sr are free to move within each void region 409, but without transferring substantial strain to neighboring void regions 409, regardless of the direction in which the steerable section is bent. Further, each void region 409 can be provided where the most strain relief is needed, and thus the strain relief portions 12sr have the most movement within the void region 409 when the steerable instrument adopts a given geometry during navigation through tortuous paths. This creates an unconstrained strain relief design such that the portion (strain relief portions 12sr) of the electrical cable 112 arranged in the void region can adapt to any geometry of the steerable instrument without causing friction between the electrical cable and the catheter substructures.

The foregoing strain relief features allow the steerable instrument 100 to bend with very small curvature without imparting substantial strain on the electrical cable 112. According to one example, a catheter body of the steerable instrument 100 can bend to a curvature as small as 5 mm (curvature having a radius of at least 5 mm) without imparting substantial strain to an EM sensor cable.

An additional aspect to the strain relief design is the tailoring of the Young's Modulus for the electrical cable assembly. The Young's modulus (or modulus of elasticity) is a mechanical property that measures the ratio of stress (force per unit area) to strain (proportional deformation) of a material in a linear elastic range of deformation. A typical value of the Young's modulus for a copper wire is in the 130 Gpa (gigapascals) region. Applying this typical value of the Young's modulus for a copper wire to the proposed design would yield a strain value of approximately 0.1% or 0.6 mm of elastic elongation for an EM sensor cable of about 550 mm of length (based upon a 550 mm length of the non-steerable section 102). In contrast, by providing the strain relief portions 12sr in the void regions 409, experimental measurements of this novel cable assembly yields a Young's Modulus of about 15 Gpa or a 0.85% strain value leading to a 4.7 mm of elastic elongation, as illustrated in FIG. 3A-FIG. 3C.

<Strain Relief and Prolapse Avoidance>

As note above, to accommodate strain conditions of the electrical cable 112 at the proximal and distal ends of the steerable instrument 100, the present disclosure considers the cable strain separately in each of the regions where strain could negatively affect the efficient steering of the steerable instrument 100. The embodiment of FIGS. 4A through 4D has explained a strain relief design of having the electrical cable 112 looped around the body of the steerable instrument 100 and free to move within void regions 409. An additional aspect to consider is the possible wire prolapse of the electrical cable 112 during movement. Wire prolapse may occur when one or more of the control wires 110 protrude from the outer surface (outer diameter) of catheter body. In this case, since the electrical cable 112 is revolved around the control wires 110, as shown in FIG. 4C-4D, the electrical cable 112 can serve as a retainer to help keep the control wires 110 in place during extreme use conditions. To that end, the electrical cable 112 may be wrapped around the control wires 110 at least one partial revolution or multiple revolutions in each void region.

Figure 5A:
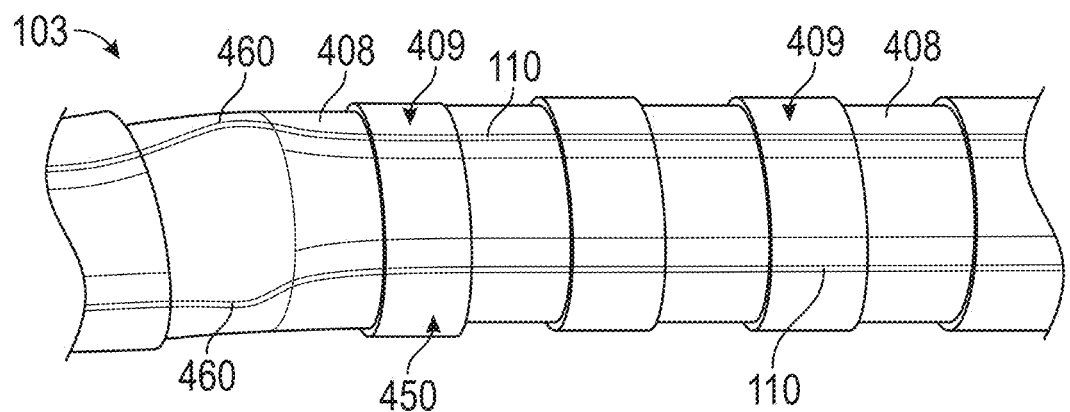
FIG. 5A shows a photograph of a steerable section 103.

FIG. 5A shows a photograph of a steerable section 103. The steerable section 103 includes a plurality of wire-guiding members 408 and a plurality of void regions 409 arranged along the length-wise direction of the steerable instrument. As can be appreciated from the photograph of FIG. 5A, one or more of the plurality of control wires 110 may tend to form one or more protrusions 460 which extend radially beyond the outer surface of the catheter body, and/or push the outer sheath 450 in the radial direction. This situation is known as wire prolapse and tends to negatively affect the efficacy of torque transmission during maneuvering of the steerable instrument. Therefore, to minimize this wire prolapse, the electrical cable 112 is at least partially secured along the wall of the wire-guiding members 408. In addition, the outer sheath 450 can be formed of reinforced weaved material to constrain the electrical cable 112 and control wires 110 within the outer diameter of the catheter body. The outer sheath 450 may be made of a mesh tube woven from, for example, synthetic resin reinforced by fiber threads. The sheath 450 may be formed by mixing, for example, a thermoplastic polyester elastomer (TPC) reinforced with inorganic fibers such as glass fibers, alumina fibers, or the like.

Figure 5B:
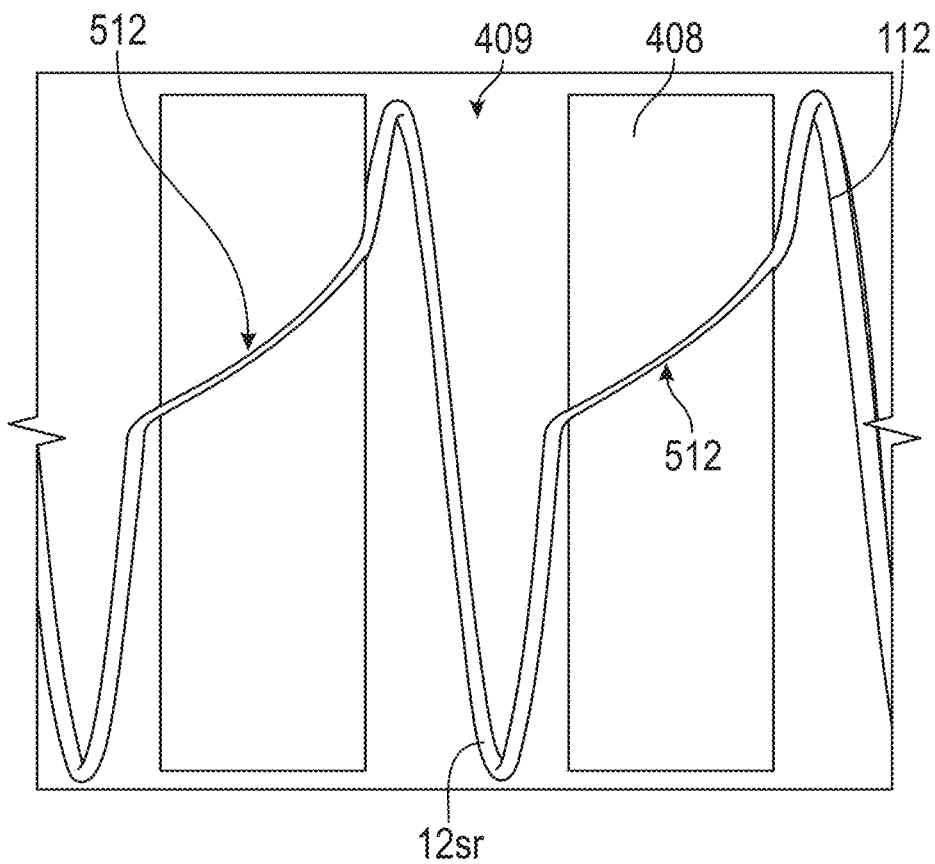
FIG. 5B and FIG. 5C illustrate two examples of a manner in which the electrical cable 112 is arranged in void regions 409 and wire-guiding members 408.
Figure 5C:
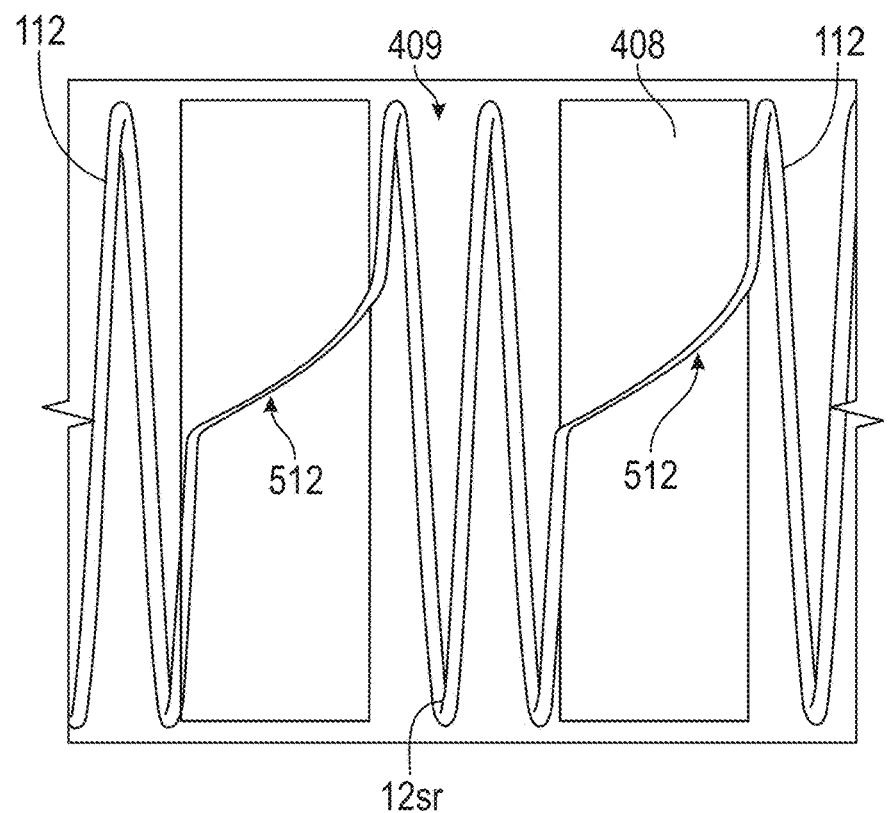

FIG. 5B and FIG. 5C illustrate two examples in which the electrical cable 112 is arranged in void regions 409 and secured onto wire-guiding members 408. FIG. 5B shows an exemplary embodiment where the electrical cable 112 is looped around the body of steerable instrument 100 to form approximately one full revolution (i.e., one turn), and then is secured in a slot or groove 512 formed along the outer surface of each wire-guiding member 408. FIG. 5C shows an exemplary embodiment where the electrical cable 112 is looped around the body of steerable instrument 100 to form about two revolutions (i.e., two turns) in each void region 409, and then is secured in a slot or groove 512 formed along the outer surface of each wire-guiding member 408. Notably, even when the electrical cable 112 is coiled multiple times in each void region 409, the electrical cable is loosely spread such that a first turn of the cable does not contact the next or second turn of the cable. This ensures free movement of the cable 112 within the void region 409 during actuation of the instrument. In addition, arranging the cable 112 in a groove 512 along the outer surface of each wire-guiding member 408 minimizes movement of the electrical cable without increasing the overall outer diameter (OD) of the steerable medical instrument 100.

Figure 8A:
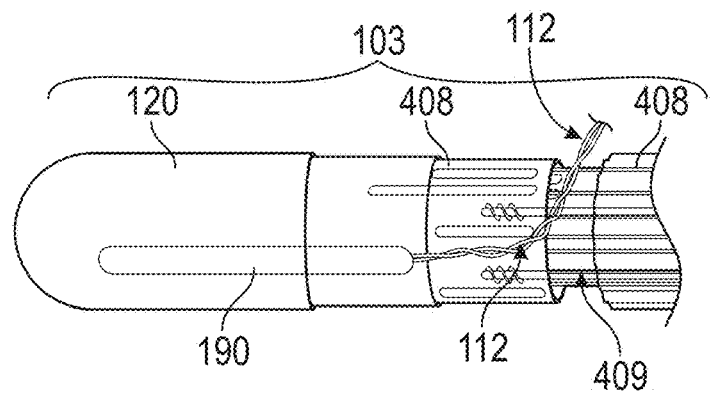
FIG. 8A, FIG. 8B, FIG. 8C, and FIG. 8D show examples of how the electrical cable 112 transitions from the catheter body substructure to a void region 409, and vice versa.
Figure 8B:
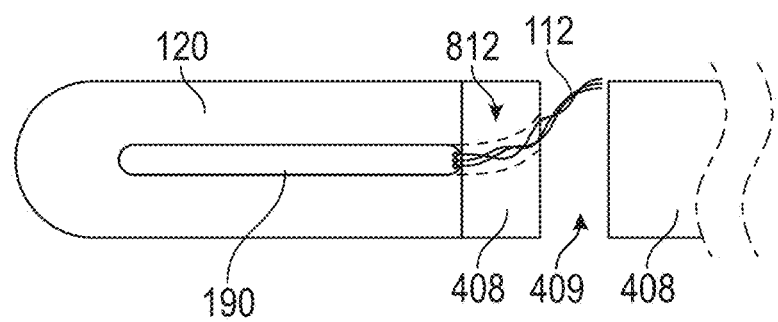
Figure 8C:
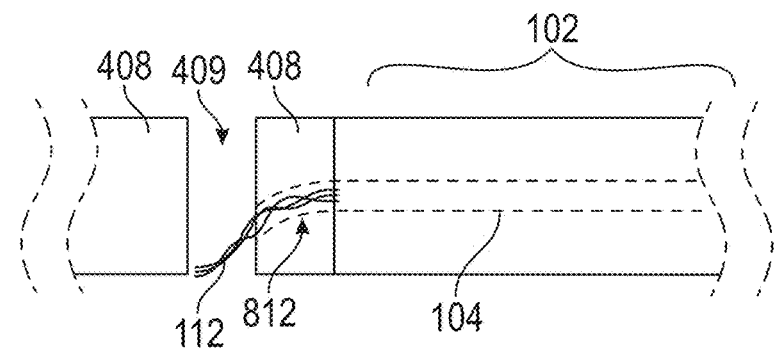

In alternative embodiments, the cable 112 could also be wrapped over the wire-guiding member itself and may be bonded at one or more points along a path similar to groove 512. In such alternative case, the wire-guiding member 408 will not have a groove or notch feature and will maintain a smooth outer surface. Additional details are shown in FIG. 8A—8C. This process of bonding the cable 112 at selective points along a path similar to groove 512 may reduce manufacturing costs. It is noted that bonding the cable 112 on the smooth outer surface of the wire-guiding member 408 may slightly increases the OD of the steerable instrument. However the strain relief feature will still work as intended because the strain relief sections ($12sr$) can be effectively isolated between neighboring void regions 409.

Figure 5D:
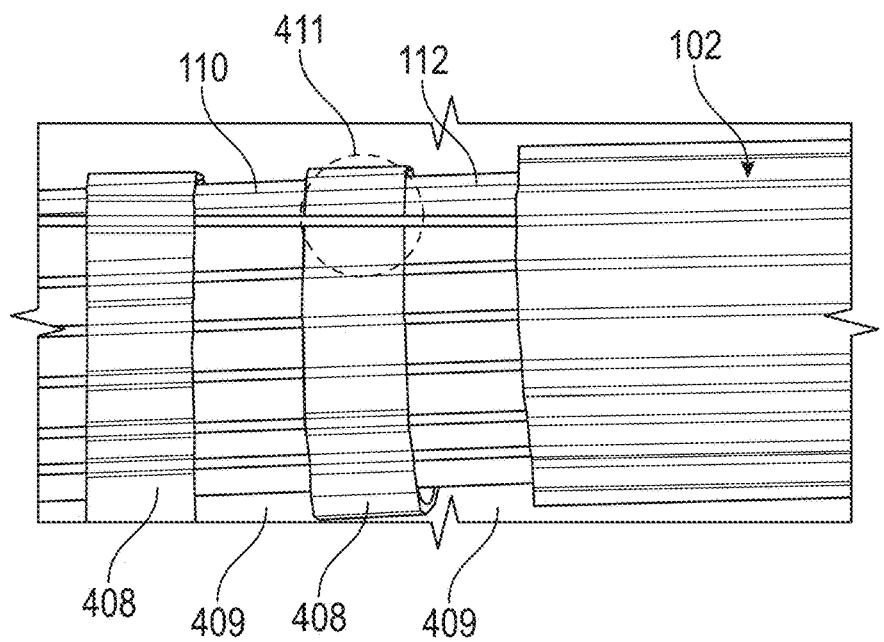
FIG. 5D shows an additional example of securing the electrical cable 112 to the wire-guiding members 408.

FIG. 5D shows an additional example of securing the electrical cable 112 to the wire-guiding members 408, in order to improve prevention of wire prolapse. FIG. 5D shows a photograph of a section of the steerable instrument 100. In FIG. 5D, the right-hand part of the photograph shows the non-steerable section (or extrusion body) 102 and the left-hand part shows part of the steerable section 103 including a plurality of wire-guiding members 408 and void regions 409. One or more of the wire-guiding members 408 (at least the first wire-guiding member 408) adjacent to the left (distal end) of the non-steerable section 102 has a lengthwise "slot" or groove on the outer surface of the wire-guiding member (like in FIG. 6B). This allows for an electrical cable 112 to be inserted into, and attached onto, the first wire-guiding member 408 at a more relaxed angle as compared to other void regions. To secure the electrical cable 112 to the wire-guiding members 408, a substructure 411 is filled with adhesive to strengthen the component and isolate cable strain forces encountered in the proximal section from being transmitted to the distal cable section. A resulting effect of this arrangement is that the electrical cable 112 transitions from the non-steerable section 102 to the first wire-guiding member 408 substantially straight, but with a certain amount of flexibility to minimize strain. This arrangement can facilitate ease of manufacturing since the electrical cable does not have to bend, and the substructure 411 can be a straight slot or groove. At the same time, since the cable is bonded to the wire-guiding members, this feature can help prevent prolapse of the electrical cable and/or control wires. After the cable 112 transitions from the non-steerable section 102 to the first wire-guiding member 408, to alleviate strain, the electrical cable can be routed around the subsequent wire-guiding members 408, as described elsewhere in this disclosure.

FIG. 6A through FIG. 6E show various details and examples of the wire-guiding members 408 applicable to any of the embodiments disclosed herein. The wire-guiding members 408 correspond to the annular shaped wire-guide member 108 shown in FIG. 2A-2B. As shown in FIG. 6A—FIG. 6E, each wire-guiding member 408 has a generally cylindrical shape (disk or ring) defined by an inner diameter (ID) and an outer diameter (OD) concentric with the longitudinal axis (Ax) of the steerable instrument 100. FIG. 6A shows an embodiment of a wire-guiding member 408 having a central opening or tool channel 105 and a slot or groove 512 formed on the outer surface of the wire-guiding member 408. In FIG. 6A, the wire-guiding member may include a plurality of wire conduits 104 similar to the wire-guiding member shown in FIG. 6B. In FIG. 6A, the groove 512 is slanted at an angle $\theta$ with respect to the longitudinal direction of the outer surface. In this embodiment, the electrical cable 112 is guided from one void region to the next along the slanted groove 112. The concept shown in FIG. 6A (the electrical cable being guided at an angle with respect to the axis Ax) may be better applicable to a situation where the cable transitions to the sensor itself and/or where the cable transitions from non-steerable section 102 to the steerable section 103. This is explained in more detail with reference to FIG. 8A-8C.

FIG. 6B shows an embodiment of a wire-guiding member 408 having a central opening or tool channel 105, a plurality of wire conduits 104 formed within the annular wall, and a slot or groove 512 formed an outer surface of the wire-guiding member. In FIG. 6B, the groove 512 is parallel to the longitudinal axis Ax (i.e., the groove 512 is formed in the longitudinal direction of the outer surface of the annular wall). Here, the electrical cable is guided from one void region to the next through the straight groove 512. FIG. 6C shows a cross-sectional view of the wire-guiding member 408 shown in FIG. 6A or FIG. 6B. Specifically, FIG. 6C shows the slot or groove 512 forms an open lumen on the outer surface of the wire-guiding member 408.

FIG. 6D shows an embodiment of a wire-guiding member 408 having a central opening or tool channel 105, a plurality of wire conduits 104, and a groove 512 formed in the inner surface of the wire-guiding member. In this case too, groove 512 can be slanted (as in FIG. 6A) or parallel with respect to the longitudinal axis Ax (as in FIG. 6B) but formed in the inner surface of the wire-guiding member. FIG. 6E shows an embodiment of a wire-guiding member 408 having a central opening or tool channel 105, a plurality of wire conduits 104, and a groove 512 formed by making a cut or channel along the length-wise direction of the wire-guiding member 408 such that the inner and outer surfaces are connected by the groove 512. In the case of FIG. 6E, for ease of fabrication, the groove 512 is a linear cut or channel joining the inner surface and outer surface of the wire-guiding member 408, and this cut extends in a lengthwise direction parallel to the longitudinal axis Ax. Naturally, a slanted cut as the groove shown in FIG. 6A is also possible.

In each of FIGS. 6A through 6E, the groove 512 is an "open lumen" or slot where the electrical cable 112 can reside when crossing over a wire-guiding member 408 to pass from one void region 409 to another neighboring void region 409. An advantage of this design is that the electrical cable is secured (coupled) to the groove 512 along the wall of the wire-guiding member 408, and therefore the electrical cable 112 does not increase the outer diameter of the catheter body as it would be the case if the electrical cable 112 were be simply wrapped over a non-slotted wire-guiding member. In addition or alternatively, the electrical cable 112 can be routed through a wire conduit 104 similar to the control wires 110. Moreover, the electrical cable 112 can be alternately routed through the wire conduits 104 of some wire-guiding members 408, and through the groove 512 (along the inner surface or outer surface) of some other wire-guiding members 408. Regardless of the manner in which the electrical cable 112 is routed from one void region to the next, it is important to minimize substantial contact between the electrical cable 112 and the catheter substructures, while also enhancing flexibility of the steerable instrument. Therefore, since the electrical cable 112 is helicoidally coiled in the void region 409, it is advantageous to route the electrical cable through a slanted or helicoidal groove 512 on the outer surface of the wire-guiding member 408 as shown in FIG. 6A (or through a groove 512 on the inner surface of the wire-guiding member 408 as shown in FIG. 6D) to minimize strain.

Figure 6F:
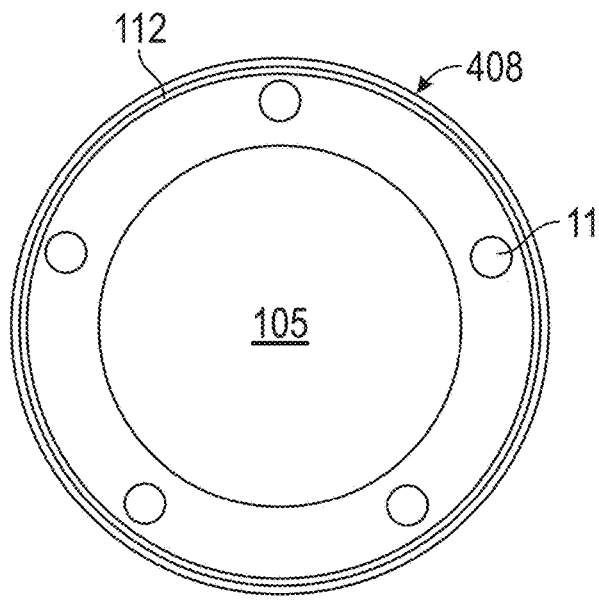
FIG. 6F, FIG. 6G, and FIG. 6H illustrate advantageous effects of arranging the electrical cable 112 in void regions 409 wrapped around the tool channel 105 and passing the electrical cable above or below or alternately above and below the control wires no.
Figure 6G:
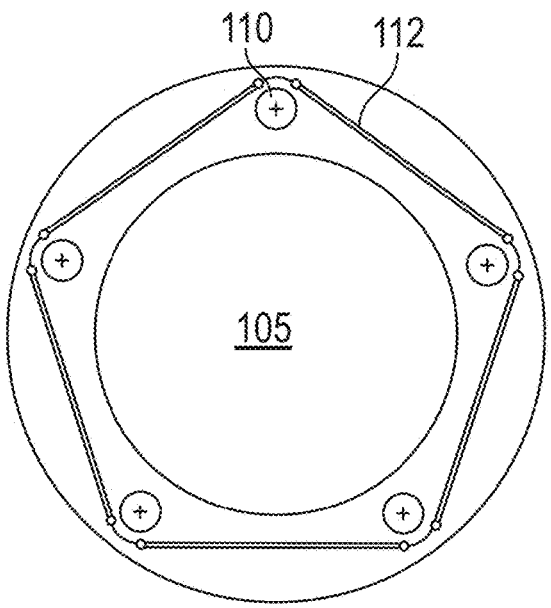

FIG. 6F and FIG. 6G illustrate an advantageous effect of arranging the electrical cable 112 in void regions 409 wrapped around the control wires 110. FIG. 6F and FIG. 6G are cross sectional views seen in the X-Y plane (the plane perpendicular to the longitudinal axis Ax). In FIG. 6F, the electrical cable 112 is looped around a plurality of control wires 110 and/or support wires 111, in a state where no tension is applied to the electrical cable 112. That is, in FIG. 6F, the steerable instrument 100 is in a non-bended state, and the electrical cable 112 is loosely arranged in a void region 409 forming a helical loop around the body of the catheter shaft. In this state, the electrical cable 112 has an amount of slack and can freely move or slide within the void region 409. On the other hand, in FIG. 6G, the electrical cable 112 is under a tension condition where the electrical cable 112 abuts or presses slightly against the control wires 110. This process illustrates an example of the electrical cable 112 meaningfully changing its "strain length" to adapt to the shape of the steerable instrument under an actuation condition. In other words, when the electrical cable 112 is subjected to a strain condition, there is space for the cable to simply reduce slack within the void region 409, and shorten the distance with respect to the control wires 110. The circular length of the electrical cable shown in FIG. 6F can adapt and "shrink" down to the length shown in FIG. 6G. In this example, a single loop of the electric cable 112 is shown; this would provide about a 5% strain relief in each void region 409. For example, the inventor's modeling of this effect under laboratory conditions showed that an initial loop of wire having a length of 9.97 mm (under non-strain condition of FIG. 6F) resulted in a final wire length of 9.47 mm under the strain condition shown in FIG. 6G. This means that the arrangement of the electrical cable 112 in the void region 419 allows for about 5% of strain relief per each wire loop in every void region 409. Since strain relief resides mainly in the distal portion of the electrical cable 112, any strain caused by actuation of the steerable section 103 is substantially isolated from cable slack or tension created at the proximal end of the steerable instrument 110. Therefore, any effect of strain caused by the electrical cable 112 within each void region 409 is substantially isolated from (not transmitted to) other sections of the cable.

Figure 6H:
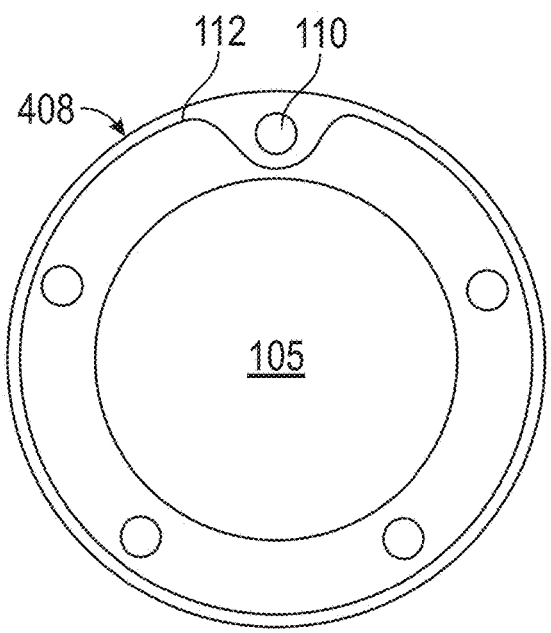

FIG. 6H shows a front view corresponding to the electrical cable arrangement shown in FIG. 4D. In the illustration of FIG. 6H, Strain relief portions of electrical cable 112 are routed underneath the control wires 110, but the electrical cable can be routed both above and below the control wires. It should be appreciated that arranging the strain relief closer to the instruments centerline Ax will reduce the strain experienced by the cable even at a maximum bending curvature. Any of the arrangements of the electrical cable 112 or combinations thereof may be used (i.e., strain relive above the control wires, strain relief below the control wires, or both above and below the control wires) to meet the end requirements of function, cost, and ease of assembly. Such options could be used with any of the strain relief designs presented (coiled around the tool channel, or folder into "S" shape longitudinally along the tool channel, etc.).

Moreover, in any of the arrangements, the electrical cable 112 can be secured (coupled) to the wire-guiding member with the use of material reflow (e.g., by reflow soldering). This process can take individual rings and "reflow" the electrical cable onto the rings and the inner sheath 430 to create a single component. In this case, the electrical cable 112 would be captive within the ring. Therefore, the strain relief portions in each void region 409 would be able to independently move within the void region during actuation and compensate for the tensile load. Alternatively, it is possible to reflow the individual rings onto the inner sheath 430, but without securing the electrical cable onto the catheter structure such that the electrical cable is not captive and allows for fluid communication of the cable between the void regions adjacent to each wire-guiding member.

<First Example of Strain Relief Elements Distributed within Catheter Substructures>

Figure 7A:
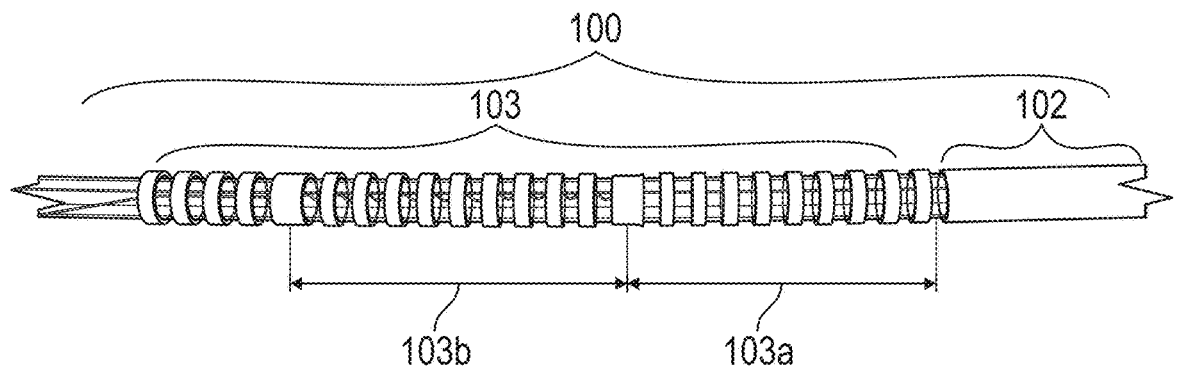
FIG. 7A, FIG. 7B, and FIG. 7C are photographs of an exemplary prototype steerable instrument 100 built according to strain relief designs of the first embodiment disclosed herein.
Figure 7B:
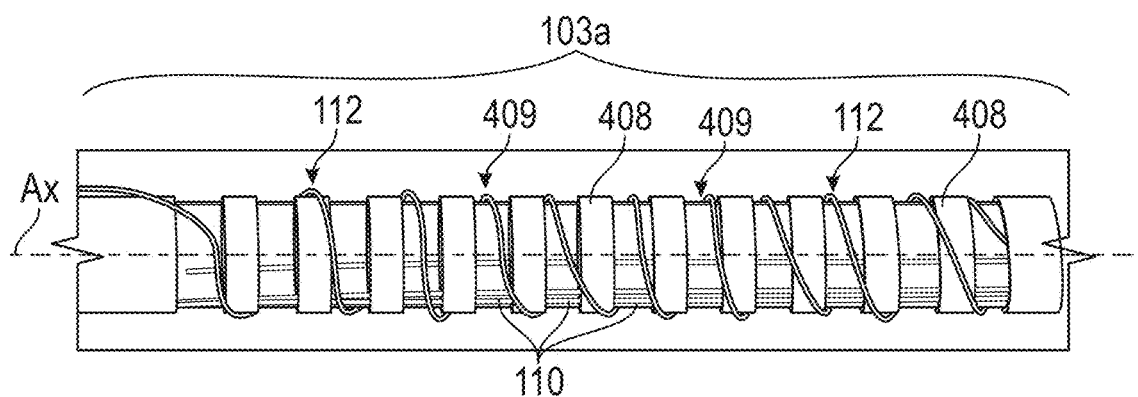
Figure 7C:
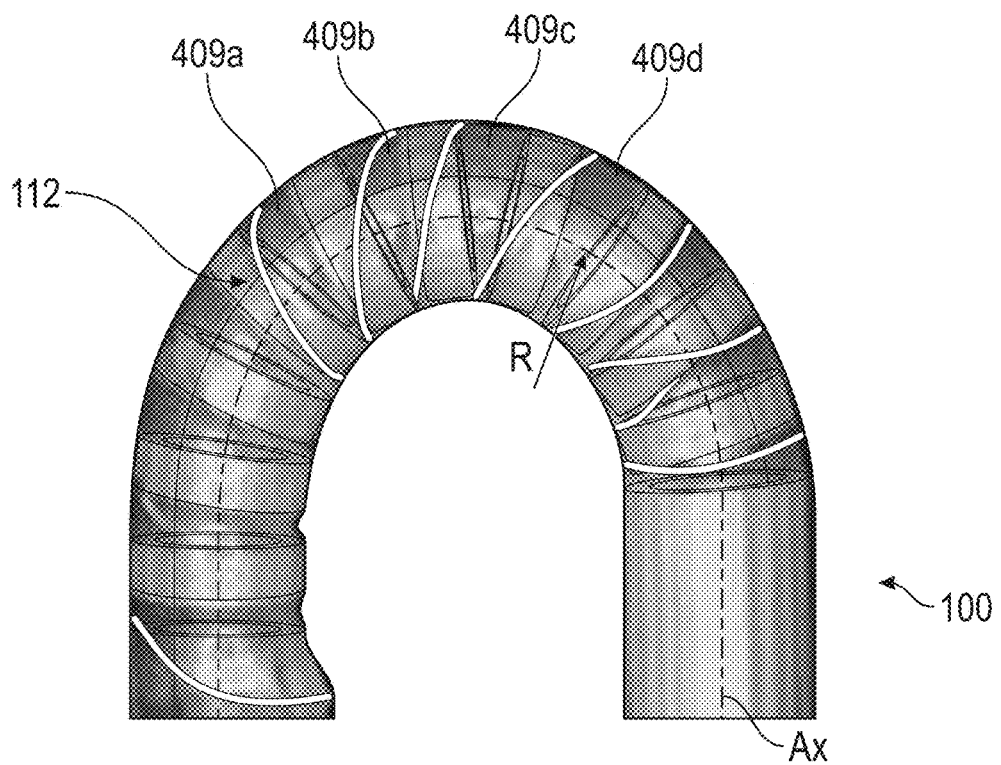

FIG. 7A, FIG. 7B, and FIG. 7C are photographs of an actual prototype steerable instrument 100 built according to the strain relief designs described in the present disclosure, according to the first embodiment. FIG. 7A is a photograph of a steerable instrument 100 having a non-steerable section 102 and a steerable section 103, in order from the proximal end to the distal end. The steerable section 103 includes a first bending segment 103a, second bending segment 103b, and possibly more bending segments. Each bending segment includes a plurality of wire-guiding members 408, as previously described with respect to other embodiments. The non-steerable section 102 is only partially shown for ease of illustration.

FIG. 7B is a photograph of a portion, segment 103a, of the steerable section 103. In FIG. 7B, the wire-guiding members 408 are arranged interposed by void regions 409 along the longitudinal axis Ax. A plurality of control wires 110 are passed through wire-conduits 104 formed in each wire-guiding member 408. An electrical cable 112 is carefully coiled around the control wires 110 in the void regions 409 and around the outer surface of the wire-guiding members 408. Preferably, the electrical cable 112 forms a full revolution (one turn) around the control wires 110 in each void region 409. In going from a first void region 409 to a second void region 409 (adjacent to the first one), the cable 112 is guided through a slot or groove 512 (see FIG. 6A and FIG. 6B) formed on the wall of each wire-guiding member 408. In this embodiment, the groove 512 is formed on the outer surface of the wire-guiding member 408 and the electrical cable 112 contacts the outer surface of the wire-guiding member 408 in a slanted manner only once. In this manner, it is possible to avoid substantial contact between the electrical cable 112 and the substructures of the steerable instrument 100. In this exemplary prototype embodiment, one or more than one electrical cables 112 can be arranged wrapped around the body of the steerable section 103, as shown in FIG. 7B. To prevent prolapse of the control wires 110, in addition to coiling the electrical cable 112 in the void regions 409, the steerable section 103 is enclosed in a flexible and substantially transparent outer sheath 450.

FIG. 7C shows a bending segment of the steerable section 103 in a bended state. As previously mentioned, the strain relief design disclosed herein allows for achieving a bending curvature of a radius (R) of at least 5 mm. To achieve such small curvatures with minimal strain on the electrical cable 112, it is advantageous to arrange a substantial portion of the electrical cable 112 in the void regions 409 with minimal contact with the catheter's substructures. More specifically, under a bending condition as shown in FIG. 7C, the portions of the cable 112 arranged in void regions 409b and 409c are configured to pull a certain amount of wire slack from the adjacent void regions 409a and 409d, respectively. Here, it should be recalled from the description of FIG. 6F and FIG. 6G, each turn of electrical cable 112 would provide about 5% strain relief. Therefore, expanding the principle of at least 5% strain relief per one revolution of cable, if one section of the catheter wire-guiding member region was subjected to a localized strain, say about 13%, the cable 112 could pull slack from the adjoining catheter "voids" to mitigate this localized strain.

<Electrical Cable Transition Between Void Regions and Catheter Substructures>

FIG. 8A, FIG. 8B, FIG. 8C, and FIG. 8D show examples of how the electrical cable 112 transitions from the catheter body substructure to a void region 409, and vice versa. For example, FIGS. 8B and 8C respectively show examples of how the electrical cable 112 transitions from a void region 409 to the distal end 120, and from the non-steerable section 102 to a void region 409. According to one embodiment shown in FIG. 8A and FIG. 8B, the electrical cable 112 is configured to establish an electrical connection between an EM sensor 190 located in the distal tip 120 and an electrical circuit (not shown) located outside (at the proximal end) of the steerable instrument 100. The photograph of FIG. 8A and drawing of FIG. 8B illustrate the electrical cable 112 undergoes a gradual transition or a bend along a curved path 812 formed in a wire-guiding member 408 before the cable begins to be coiled in the void region 409. Using FIG. 4A as reference, this bend also happens while the electrical cable 112 is routed through a feature component or wire-guiding member of an inflection point 107. The feature for providing a cable transition from one catheter substructure to a void region 409, or a transition from a void region 409 to a catheter substructure, may be implemented using the slot or groove 512 shown in FIG. 6A. A similar transition may also be achieved using the groove 512 shown in figures: FIG. 6B through FIG. 6E. After the electrical cable 112 is routed in the manner shown in FIGS. 8A and 8B, the cable 112 may then be bonded in place afterwards. This gradual bending transition keeps the cable 112 from otherwise having an acute bend angle (of say 90 degrees or more) which could lead to an open circuit condition. In other words, to minimize the strain condition of electrical cable 112, it is advantageous to provide a cable transition from a catheter substructure to a void region, and/or from a void region 409 to a catheter substructure, at an angle theta (θ) grater than zero degrees and smaller than 90 degrees.

Figure 8D:
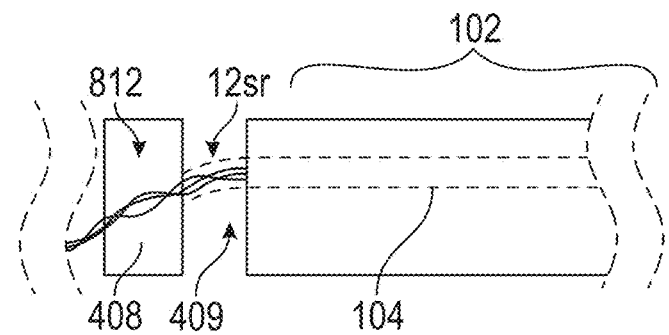

FIG. 8C shows the same principle of routing the electrical cable 112 from a catheter substructure to a void region 409 through a curved path 812 at an angle greater than zero degrees and less than 90 degrees but with the transition taking place before the cable exits the wire conduit 104. In FIG. 8C, the electrical cable 112 is first passed from the proximal end of the non-steerable section 102 to the steerable section 103 via a wire conduit 104 (wire lumen) formed within the wall of the tubular shaft (extrusion body in FIG. 3C). Specifically, at the distal end of the non-steerable section 102, before the electrical cable 112 exits the wire conduit 104, the conduit takes a slightly curved or inclined path 812. This feature path 812 can be formed in the shaft of the non-steerable section 102 or by joining (bonding) a wire-guiding member 408 to the distal end of the non-steerable portion 102. Alternatively, as shown in FIG. 8D, the electrical cable 112 enters the feature curved path 812 after the electrical cable exits the lumen at the distal end of the non-steerable section 102. In FIG. 8D, the electrical cable 112 forms a strain relief portion 12sr which is a portion of the electrical cable less than one full revolution in a first void region 409 before entering into the wire-guiding member 408. This arrangement has the same benefit described above with respect to FIGS. 8A and 8B. In addition, FIG. 8B can also be modified such that the electrical cable 112 enters into the distal end 120 after exiting from the last wire-guiding member 408 and traversing a last void region 409. In other words, the implementation and advantages of the transition of electrical cable 112 applies to both a transition from the steerable section 103 into the distal end 120, and a transition from the non-steerable section 102 into the wire-guiding members 408 of the steerable section 103.

<Strain Relief Elements Providing Slack in Void Regions of Steerable Section>

Figure 9A:
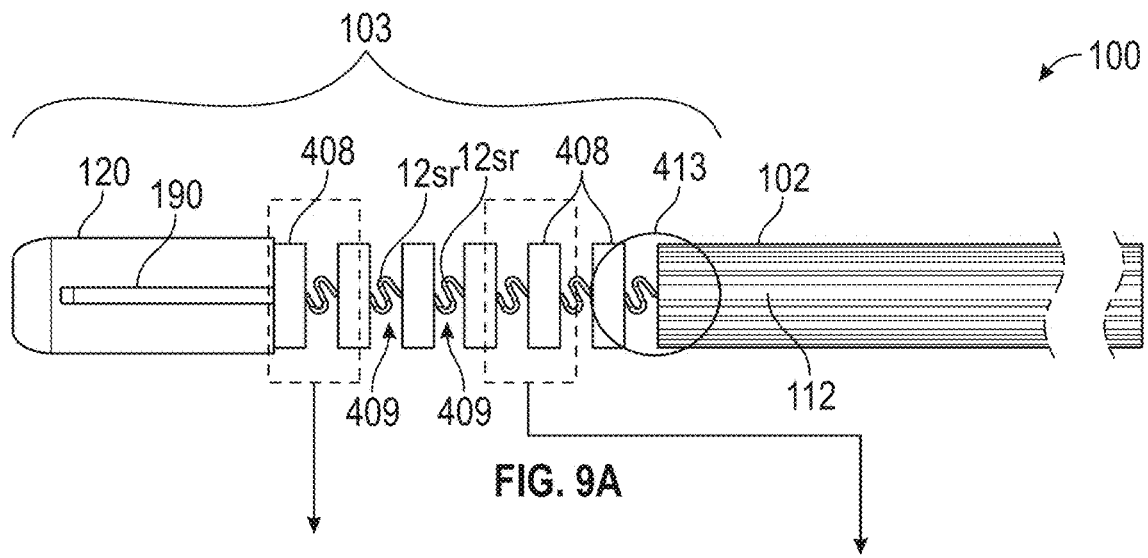
FIG. 9A, FIG. 9B, FIG. 9C, FIG. 9D, and FIG. 9E illustrate various details of a strain relief design for a portion of an electrical cable 112 arranged in the steerable section 103 of the steerable instrument 100, according to a second embodiment.

FIG. 9A, FIG. 9B, FIG. 9C, FIG. 9D, and FIG. 9E illustrate various details of a strain relief design for a portion of the electrical cable 112 arranged in the steerable section 103 of the catheter body. FIG. 9A illustrates the general structure of a simplified version of the steerable instrument 100. As described above, the steerable instrument 100 includes a distal steerable section 103 and a proximal non-steerable section 102.

As shown in FIG. 9A, the instrument 100 incudes the non-steerable section 102 (an extrusion body region) and the steerable section 103, in this order from the proximal to the distal end. The steerable section 103 includes an anchor point 413, a region comprised of a plurality of wire-guiding members 408 (wire-guiding disks), a distal end or tip region 120, and a plurality of void regions 409 interposed between the wire-guiding members 408. Along the length of the steerable instrument 100, control wires no, support wires 111, and electrical cables 112 are arranged within the wall of the tubular shaft offset from the instrument axis Ax (as explained above with respect to FIG. 1A and FIG. 1B).

In the disk region of the steerable section 103, the electrical cable 112 advances through a wire conduit 104 of each wire-guiding member 408. In order to provide a certain amount of slack, the electrical cable 112 is arranged to form one or more strain relief portions 12sr having an "S" shape, in at least one of the void regions 409. The "S" shape is achieved by folding a portion of the electrical cable; the folded portion is such that it can provide enough slack for maximum bending of the instrument, but without coming into contact with the control wires no. In this manner, the electrical cable 112 incorporates at least one strain relief portion 12sr having an "S" shape in at least one of the void regions 409. The strain relief portions 12sr (strain relief elements) are not limited to the void regions 409; these strain relief portions can potentially extend to within the catheter disks or catheter substructures (e.g., guiding members and anchor members shown in FIG. 2A) of the steerable instrument 100. Disposing the strain relief portions 12sr of electrical cable 112 in the void regions 409 allows for the steerable instrument 100 (catheter or endoscope) to bend to a desired curvature without imparting any strain to the electrical cable or on the electronic device (e.g., an EM sensor) powered by the electrical cable. The anchor point 413 refers to a region of the steerable instrument 100 where the electrical cable would be anchored (potentially selectively) to the catheter extrusion body allowing for the isolation of cable strain forces encountered in the proximal section from being transmitted to the distal cable section.

Figure 9B:
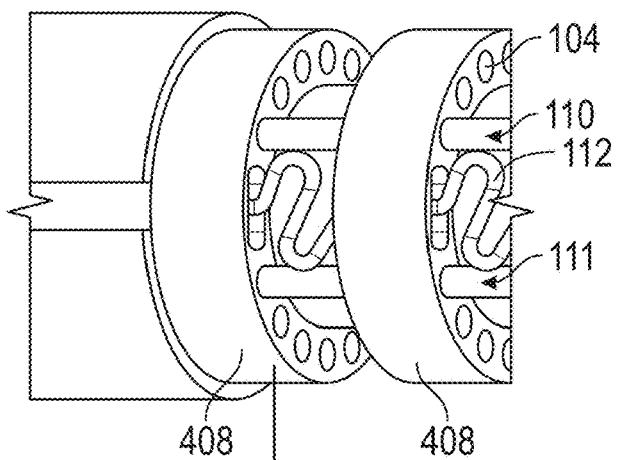
Figure 9C:
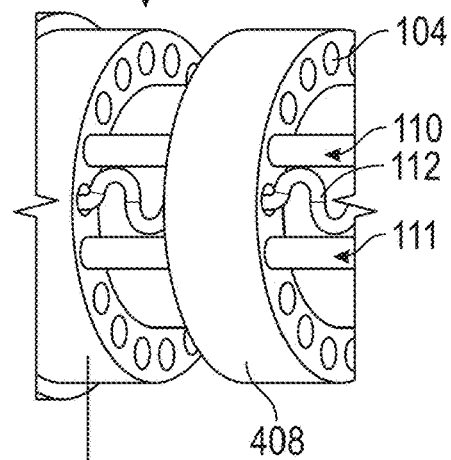

From FIGS. 9A, 9B, and 9C, it can be appreciated that the strain relief design disclosed herein is a non-constrained design in that the strain relief portions 12sr do not actively contact any surface of the wire-guide members 408. In contrast, a constrained strain relief design is one in which the wires/cable have meaningful contact with other structures or substructures of the steerable instrument. In a steerable instrument 100 of reduced outer diameter, the delicate electrical cables 112 (EM cables), even under normal operating conditions, would undergo high strain (e.g., about 28%+ strain) during steering operations, but should not be subjected to tensile forces above a predetermined tolerance force (e.g., approximately 1.8 Newton).

In order to effectively mitigate strain conditions in the electrical cable 112, the friction between the electrical cable 112 and any other structure of the steerable instrument 100 needs to be minimized. This is most notably true for delicate structures where friction levels even in fractions of a Newton can be meaningful. The reason for this is that, in delicate medical devices, friction leads to inhibited flexibility. For example, in steerable catheter or endoscopes of a minimized diameter, as the force to bend the steerable instrument to a given geometry increases, even a slight friction of the electrical cables can hinder the normal operation of the catheter. Additionally, frictional forces beyond a predetermined strain (e.g., higher than 1.8 Newton) could result in damage or failure of the electrical cable itself. Also, friction of the electrical cable with the catheter structures can cause a "pinch point" effect to develop in the cable, and this effect can create a sharp bend during catheter use. This pinch point effect can also lead to an open circuit condition if the electrical cable becomes damaged. Therefore, the "void regions" 409 pictured in FIG. 9A, FIG. 9B, and FIG. 9C are designed with specific dimensions (e.g., 1 mm width at 1 mm intervals), which is important to the overall design of the steerable instrument 100. More specifically, the void regions 409 and the specific dimensions thereof enable minimal contact between the electrical cable 112 and other structures of the steerable instrument 100. Further, each void region 409 is a region of the catheter where the most strain relief resides, and thus the strain relief portions 12sr have the most movement within the void region 409 when the steerable instrument adopts a given geometry during navigation through tortuous paths.

FIG. 9B shows a more detailed view of the disk region close to the catheter tip or distal end 120. As shown in FIG. 9B, the wire-guide members 408 at the distal region (near the tip of the catheter) have an enhanced feature. The enhanced feature is a non-circular lumen 404b. In this case, the electrical cable 112 passes through the non-circular lumen 404b with sufficient space between a control wire no and/or a support wire 111. The non-circular lumen 404b enables the electrical cable 112 to have more slack and less strain, in particular when catheter tip 120 is controlled in a lateral type motion (R in FIG. 11) while imparting less strain on the electrical cable 112.

FIG. 9C shows a more detailed view of the disk region close to the non-steerable section 102. In the disk region close to the non-steerable section 102, the electrical cable 112 travels through a circular lumen 104 similar to the near control wire no and support wire 111. The region in the middle of the steerable section 103 has wire-guide members 408 in a similar fashion as shown in FIG. 9C (i.e., with less space between the electrical cable 112 and the nearby control and support wires 110 and in, respectively).

Figure 9D:
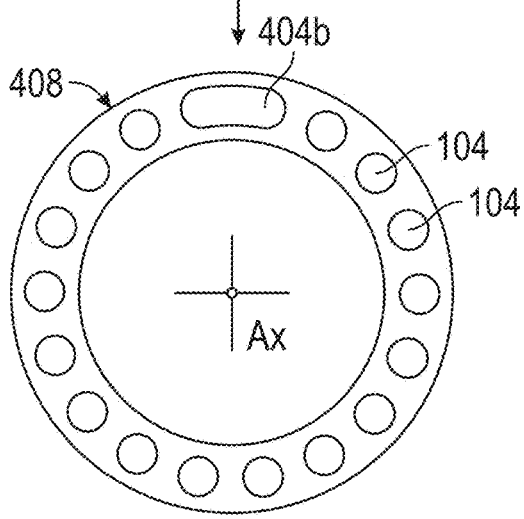
Figure 9E:
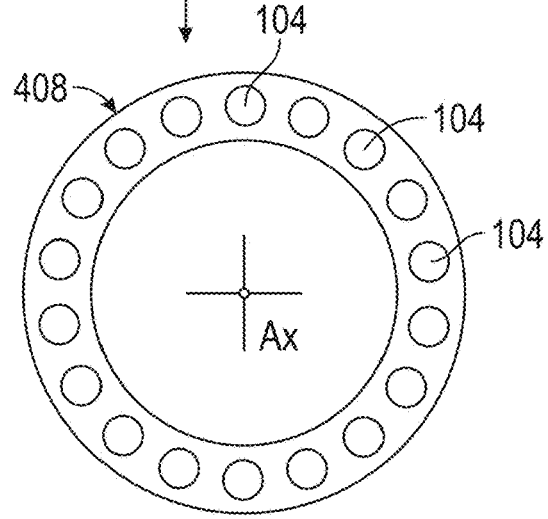

FIG. 9D shows a front view of a wire-guide member 408 used near the catheter tip 120. This wire-guide member 408 has a plurality of circular wire lumens 404a and one or more non-circular lumen 404b. As explained above, the non-circular lumen 404b is a feature which enables the catheter tip to maneuver in a lateral type motion while imparting less strain on the EM cable. FIG. 9E shows a front view of a wire-guide member 408 used near the non-steerable section 102. This wire-guide member 408 has a plurality of circular lumens 404a, but does not include the non-circular lumen 404b. As explained above, it is important to isolate the strain applied to the electrical cable 112 in the distal section of the steerable instrument from the strain applied to the proximal region of the electrical cable. Therefore, when the non-circular lumen 404b is not used in the wire-guiding members 408 near to the anchor point 413, the strain generated by a lateral motion of the catheter tip is not transferred to the proximal region of the cable.

An additional aspect to the strain relief design is the Young's Modulus of the electrical cable assembly. The Young's modulus (or modulus of elasticity) is a mechanical property that measures the ratio of stress (force per unit area) to strain (proportional deformation) of a material in a linear elastic range of deformation. A typical value for Young's modulus of a copper wire is in the 130 Gpa (gigapascals) region. Applying this typical value for Young's modulus of a copper wire to the proposed design would yield a strain value of approximately 0.1% or 0.6 mm of elastic elongation for an EM cable of about 550 mm of length (based upon a 550 mm length of the non-steerable section 102). In contrast, by providing the strain relief portions 12sr in the void regions 409, experimental measurements of this novel cable assembly yields a Young's Modulus of 15 Gpa or a 0.85% strain value leading to 4.7 mm of elastic elongation.

Figure 10:
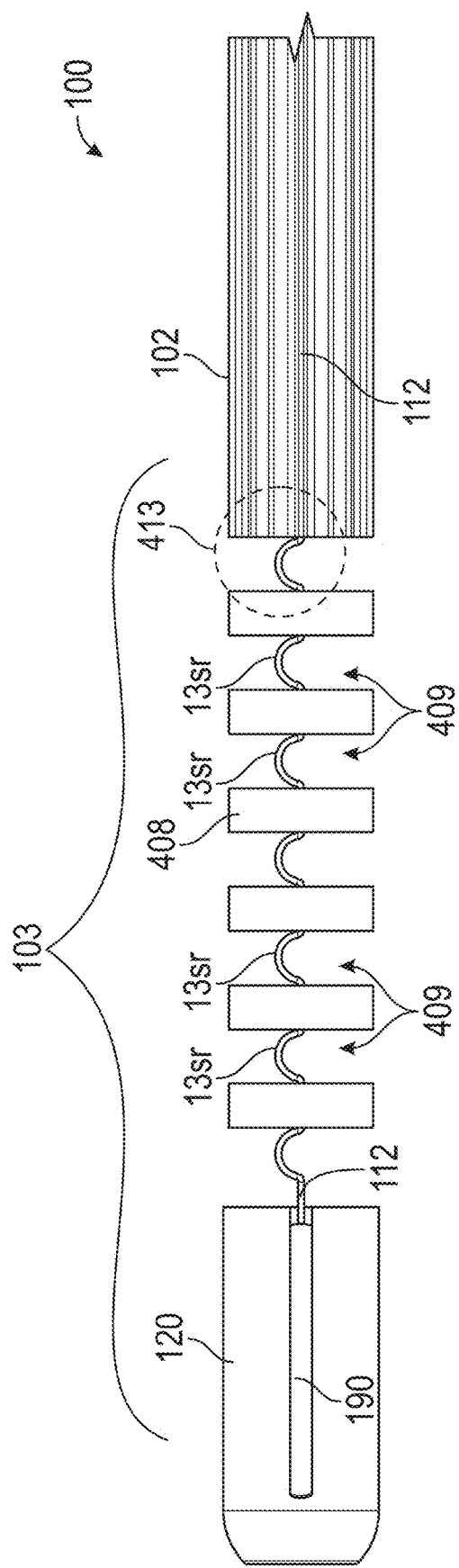
FIG. 10 illustrates another embodiment of the steerable instrument 100 including a proximal non-steerable section 102 and a distal steerable section 103 with electrical cable strain relief components.

FIG. 10 illustrates another embodiment of the steerable instrument 100 including a distal steerable section 103 and a proximal non-steerable section 102. Similar to the embodiment shown in FIG. 9A, the steerable section 103 includes an anchor point 413, a disk region comprised of a plurality of wire-guiding members 408 (wire-guide member), a distal end or tip region 420, and a plurality of void regions 409. Along the length of the steerable instrument 100, control wires no, support wires in, and electrical cables 112 are provided within (inside) the wall of tubular shaft offset from the instrument axis Ax (as explained above with respect to FIG. 1A and FIG. 1B). In the disk region of the steerable section 103, the electrical cable 112 advances through wire conduits or lumens 404. To provide a certain amount of slack, the electrical cable 112 is arranged to from strain relief portions 13sr having a "C" shape, in each of the void regions 409. That is, the strain relief portions 13sr of electrical cable 112 are formed in at least one of the void regions 409. The strain relief portions 13sr shown in FIG. 10 have a "C" shape, as opposed to an "S" shape as illustrated in FIG. 9A.

Naturally, the strain relief portions 12sr shown in FIG. 9A and strain relief portions 13sr shown in FIG. 10 can be combined to form a further alternative embodiment. Specifically, an embodiment can be envisaged in which the strain relief portions 12sr having an "S" shape are provided in a region of the steerable section where higher strain relief is desired, and strain relief portions 13sr having a "C" shape are provided in a region of the steerable section where lower strain relief is desired. Further, the strain relief portions 12sr and 13sr can be arranged alternately in a patterned order. Moreover, since electrical cables are highly malleable, the strain relief portions are not limited to "S" or "C" shaped portions of wire. The strain relief portions can take any shape or arrangement (e.g., S, C, Z, etc.) as long as a portion of the electrical cable is arranged in one or more void regions 409 to provide a certain amount of slack for mitigating the tension load applied to the electrical cable when the catheter body is bent during instrument operation.

<Strain Relief Elements Providing Slack at Proximal End of Non-Steerable Section>

Figure 11:
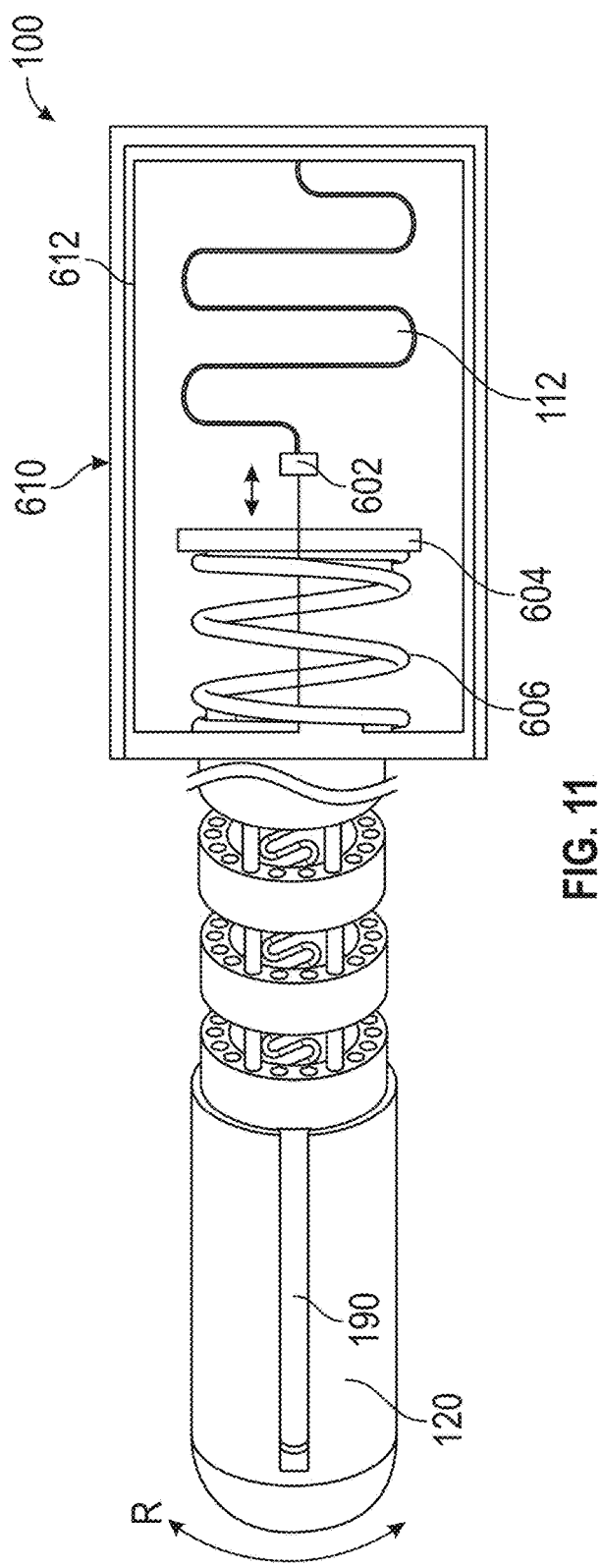
FIG. 11 illustrates an embodiment of the steerable instrument 100 comprising a strain relief mechanism 610 disposed at or connected to the proximal end of the instrument.

As note above, to accommodate strain conditions of the electrical cable 112 both at the proximal and distal ends of the steerable instrument 100, the present disclosure considers the strain separately in each of the regions where strain could negatively affect the efficient steering of the steerable instrument 100. FIG. 11 illustrates an embodiment of the steerable instrument 100 where the strain condition of the electrical cable 112 is considered at the proximal end of the steerable instrument.

In FIG. 11, a strain relief mechanism 610 may include a portion or may be part of the handle 200 (e.g., it can be a terminal, socket or connector 612) which houses therein the cable strain relief feature. Specifically, the strain relief mechanism 610 may incorporate a connector 612 (connector mechanism) that will not bias the electrical cable 112 in a proximal direction when the catheter is straight (in a non-actuated condition), and thus the electrical cable 112 will not create any strain condition. However, when the steerable instrument 100 is bent in a lateral direction R, a displacement of the electrical cable 112 is made in the distal direction proportionally to the amount of lateral bending. In this case, a cable stop mechanism 602 is configured to abut against a retainer element 604. The retainer element 604 compresses a spring 606 as the electrical cable moves distally inside the catheter body. These actions will then bias the electrical cable 112 in a proximal direction due to the compressive action of the spring 606. Then, when the catheter is again straightened, the spring 606 will pull at least part of the slack of the electrical cable 112 back out of the catheter body. The strain relief mechanism 610 can be purely mechanical, and by the action of the spring and retainer element, the strain relief mechanism can add and/or remove electrical cable slack from the catheter body. In at least some embodiments, the strain relief mechanism 610 can be controlled by the system controller 302 and/or CPU 410 of the computer system 400 so that slack of the electrical cable may be automated. For example, as described with reference to the configuration and operation of a steerable medical instrument, the system continuously monitors the contact force that is exerted by the catheter tip by using the sensor system of sensors 304. In this regard, the sensor signal 305 from the sensors 304 can be used by the controller 320 and/or computer system 400 to control the strain relief mechanism shown in FIG. 11.

This feature of an external strain relief mechanism can advantageously alleviate the potential condition where the cable slack left in the lumen "binds up" and inhibits the catheter maneuverability and/or causes an open circuit condition. Moreover, since slack in the distal portion of the electrical cable 112 is substantially isolated from the possible slack created at the proximal end, any effect of strain caused by the electrical cable within the connector mechanism is not transmitted to the remainder of the cable.

<Second Example of Electrical Able with Strain Relief Elements within Catheter Body>

Figure 12A:
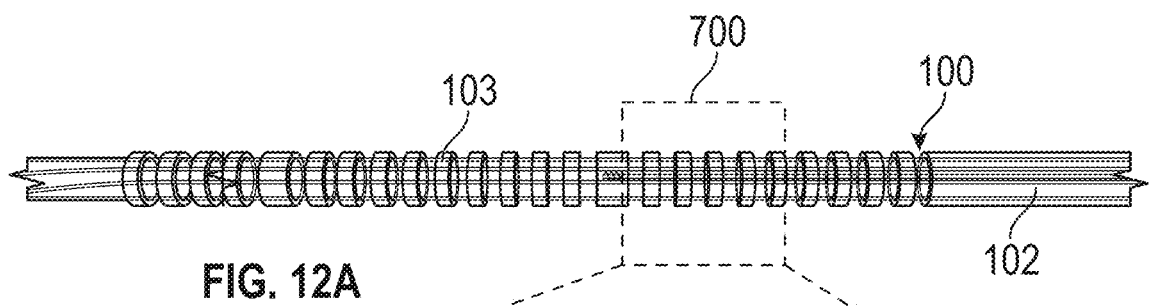
Figure 12C:
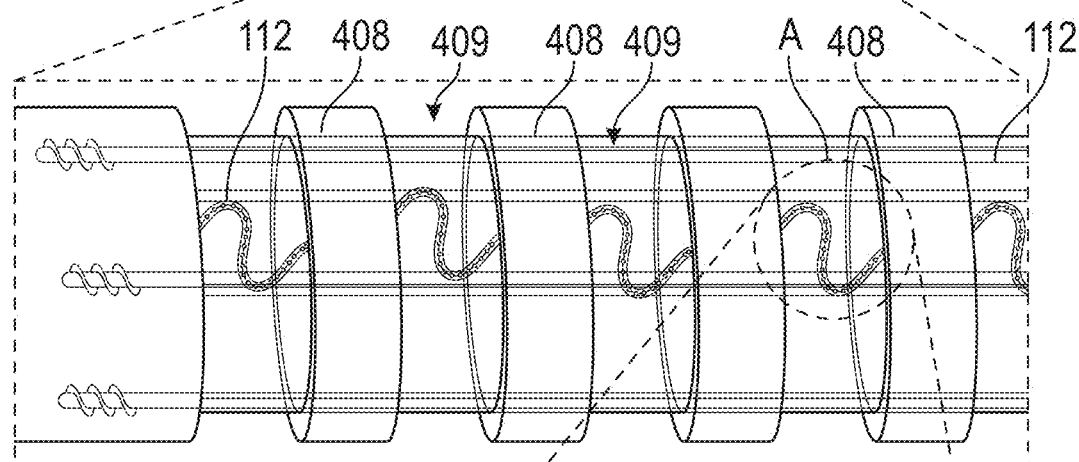
Figure 12C:
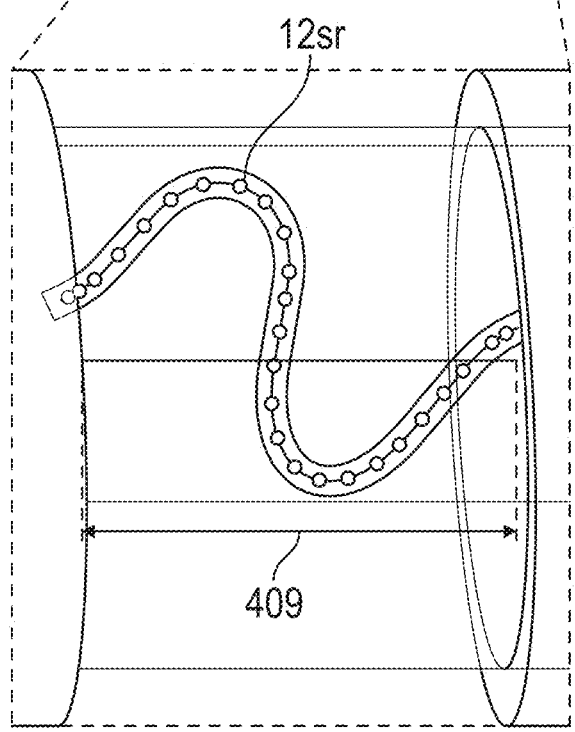

FIG. 12A, FIG. 12B, and FIG. 12C are photographs of an actual prototype steerable instrument 100 built according to strain relief designs described according to a second embodiment of the present disclosure. FIG. 12A is a photograph of a steerable instrument 100 having a non-steerable section 102 and a steerable section 103. FIG. 12B is a zoomed photograph of a portion 700 of the steerable section 103, and FIG. 12C shows a zoomed photograph (inset A) of a strain relief element arranged in void region 409. In this example prototype embodiment, one or more than one electrical cable 112 is arranged along (inside) a wire-conduit on the wall the non-steerable section 102 at the proximal end of the instrument 100. In the steerable section 103, the electrical cable 112 advances through a cable lumen or wire conduit 104 of each of a plurality of wire-guiding members 408. As shown in the detail of inset A in FIG. 12C, in each void region 409, the electrical cable 112 forms a strain relief portion 12sr by being folded into an "S" shape. This design allows for approximately 44% strain relief of tension load applied to the EM wire without causing any interference to the normal operation of the steerable instrument 100.

<Electrical Cable with Strain Relief Elements Offset with Respect to Instrument Axis>

Figure 13:
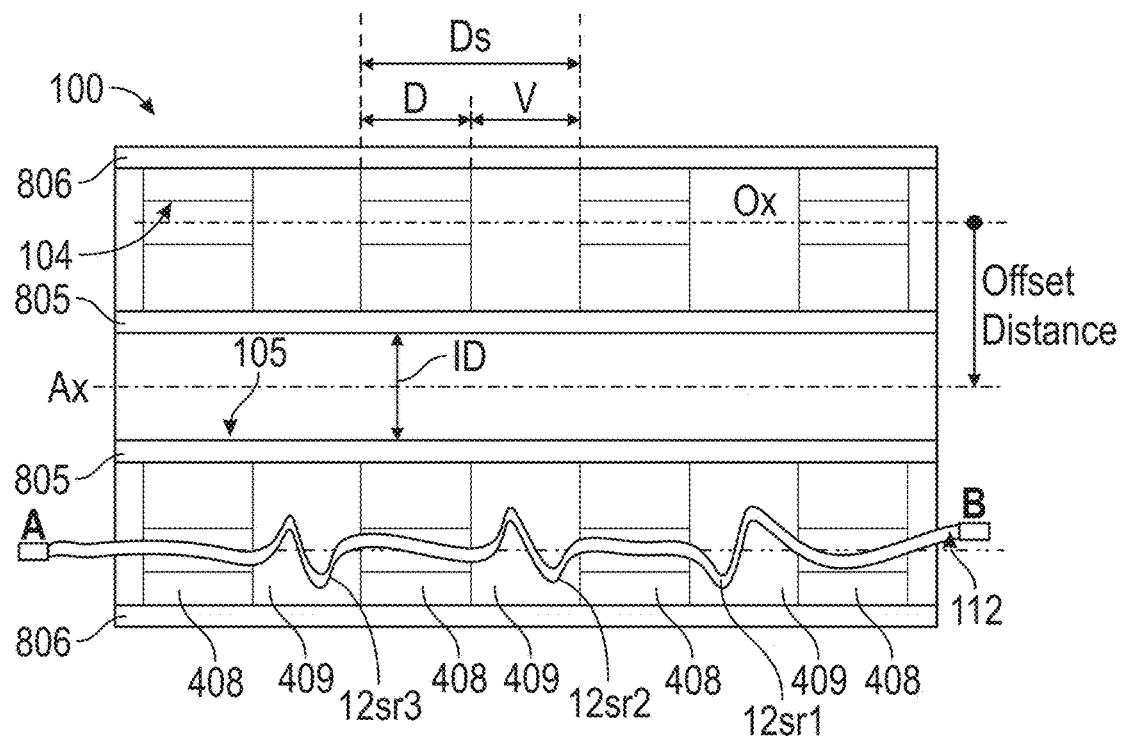
FIG. 13 illustrates a sectional view along the longitudinal axis Ax of steerable instrument 100 comprising a plurality of wire-guiding members 408 and void regions 409 in a portion of the steerable section 103.

FIG. 13 illustrates a longitudinal sectional view along the longitudinal axis Ax of a portion of the steerable section 103 (disk region) of the steerable instrument 100. As illustrated in FIG. 13, the steerable section 103 of steerable instrument 100 includes an inner sheath 805 and an outer sheath 806 arranged concentrically to each other around the instrument central axis Ax. Contained between the inner sheath 805 and the outer sheath 806 are a plurality of wire-guiding members 408 arranged at a predetermined pitch distance (Ds) such that each wire-guiding member 408 is separated from another structure by a void region 409. The inner sheath 805 defines the inner diameter (ID) of the at least one channel (tool channel) 105. Each of the wire-guiding members 408 has a plurality of through holes or wire-conduit 104 aligned in a lengthwise direction along an axis Ox. The axis Ox is substantially equidistant and offset from the instrument axis Ax. However, the void regions 409 are concentric with the instrument axis Ax. That is, FIG. 13 shows the catheter disk region lumen geometry centerline is offset with respect to the instruments axis Ax by an "offset distance". On the other hand, the axis of the void regions 409 (catheter void geometry centerline) is the same as the instrument axis Ax (catheter's central axis). In one embodiment, the wire-guiding members 408 measure about 1 mm in width (D) and are arranged at about 1 mm distance (V). That is, the wire-guiding members 408 or void regions 409 are arranged at predetermined pitch distance or intervals (Ds).

In FIG. 13, an exemplary electrical cable 112 is shown as disposed along a wire-conduit 104 and passing through two points A and B along the wall of the steerable section 103 of the instrument 100. In this arrangement, point A and point B are locations (portions) along the electrical cable 112 which are constrained (affixed) will not move relative to each other even when the steerable section 103 is bent to form one or more curvatures within a biological lumen. More specifically, when the instrument 100 bends, the strain relief sections 12sr1, 12sr2, 12s3, etc. (first portions of the electrical cable), each arranged in a void region 409 will provide a certain degree of slack to allow the electrical cable 112 to not undergo strain between the electrical cable portions affixed at point A and point B. That is, point A and point B of the electrical cable 112 may not slide relative to the conduit 104. However, there may be some movement of the electrical cable in certain portions between the two points A and B. For example, when the instrument 100 bends, a first strain relief section 12sr1 could stretch to a point where the strain relief section becomes straight and can pull on the second strain relief section 12sr2, and so on. However, the number of strain relief sections can be predetermined (e.g., based on a maximum expected bending of the steerable section) such that the electrical cable 112 will experience minimal strain (or no strain at all) between point A and point B.

<Function of Strain Relief Elements on Image Guided Navigation of Steerable Instrument>

Figure 14:
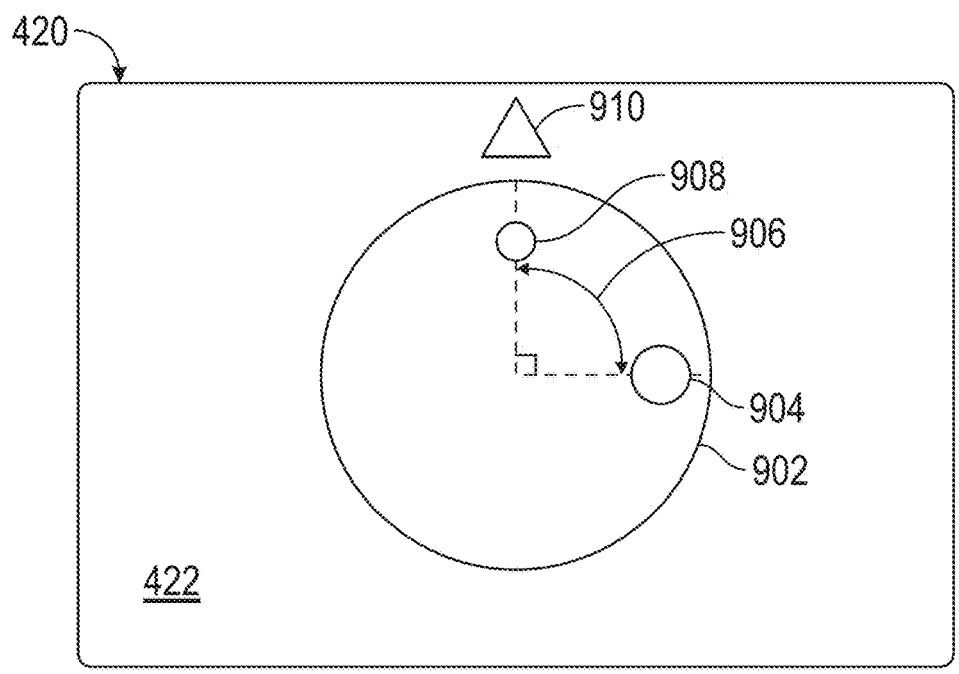
FIG. 14 shows an exemplary display device configured to display a sensor orientation indicated by a marker displayed on a monitor screen.

FIG. 14 shows an exemplary display device 420 (mentioned in FIG. 1A) configured to display a sensor orientation represented by a marker either virtually or physically displayed on a monitor screen 422. As mentioned above, electrical cables 112 are provided in wire conduits 104 of the steerable instrument 100 to connect a power source terminal to one or more electronic devices included within the body (e.g., EM sensors, camera, LEDs) or/and end-effector tools provided at the distal end of the endoscope or catheter instrument. In one example, electrical cables 112 can be connected to an EM sensor 190 and/or to an imaging device (camera) 180 mentioned in FIG. 1B. Then, during a procedural use of the steerable instrument 100, at least one sensor which has a location that is offset from the catheter's central axis and oriented perpendicular to a patient table can be used to track the position and/or orientation of the steerable section 103 of instrument 100. In that case, the sensor orientation can be processed by the CPU 410 and displayed represented by a marker 910 either virtually or physically displayed on a monitor screen 422 of display device 420, as shown in FIG. 14. In addition, a lumen image 902 acquired by camera 180 can display a camera position 904, clocking orientation markers 906, and a sensor position 908.

As described in the foregoing embodiments, the lumen or wire-conduit 104 through which the electrical cable 112 is routed has several enhanced features which are distinguishable over known designs. In previously known designs, the electrical cable lumen geometries are substantially uniform from one end to the other of the steerable instrument sheath, and the electrical cable generally interacts (contacts) in a significant manner with the substructures of the catheter or endoscope.

In contrast, according to the various embodiments described above, the structure of the lumen geometry changes according to the sections of the instrument where strain relief is most necessary. For example, as illustrated in FIG. 5B-5C, FIG. 7A-7C, FIG. 8A-8D, etc., the steerable instrument 100 can have a plurality of distinct portions of the steerable section where strain relief can be made different from each other. Each section has different space constraints due to the increased number of support and drive wires. Providing equal amounts of strain relief throughout the length of the steerable section 103 may not address the cumulative strain relief needed for the entire passive wire guide region. To achieve the desired strain relief result, it is important to specifically allocate strain relief to the sections of the instrument that need most. Each region has a unique set of design requirements, and thus each region must incorporate different design elements. Therefore, according to the present disclosure, different strain relief regions are intended to be isolated from each other such that, for example, electrical cable strain forces encountered in the proximal region of the instrument do not transfer to the same electrical cable in the distal region of the instrument and vice versa.

The electrical cable relief design described above can provide some remarkable advantageous effects to a steerable instrument including, but not limited to, the following. A multi-geometric (and potentially uni-geometric) catheter lumen routed with an electrical cable assembly attached to an electromagnetic (EM) sensor with a sensor axis offset between 0.1 to 3.0 mm (1.4 mm preferred) from the catheter central axis. At least a portion of the cable lumen is offset between 0.1 and 3.0 mm (1.4 mm preferred) from the catheter central axis. The cable lumen axis (lumen axis defined by the lumen geometric centroid) of the electrical cable changes from offset to coaxial with the length of the catheter body. The lumen axis Ox offset repeats in a patterned order (at least partially). The pattern repeats (at least partially) between 0.1 and 3.0 mm (2.0 mm preferred).

At least one lumen geometry has strain relief elements disposed within the lumen itself. The lumen geometry for the electrical cable includes a non-circular opening, wherein the electrical cable can have slack inside and outside the non-circular opening. At least a portion of higher strain relief is located in a distal section of the catheter, and lower strain relief is located at or near the proximal section of the catheter.

The steerable instrument includes a wire lumen geometry configured to guide an electrical cable therethrough, where at least one portion of the electrical cable can have a Young's modulus in a range of 2-25 gigapascals (Gpa) and more preferably 15 Gpa.

At least one lumen geometry is non-circular and substantially symmetric about the instrument central axis. At least one lumen geometry revolves around the instrument central axis between 60 and 360 degrees (360 degrees preferred).

The steerable instrument includes at least one sensor at a location that is offset from the catheter central axis and oriented perpendicular to a patient table during a procedural use. The sensor orientation can be indicated by a marker either virtually or physically displayed on a monitor of the system.

The steerable instrument includes a handle with a strain relief mechanism configured to add or remove electrical cable slack to/from the cable lumen. The strain relief mechanism is located in the proximal section of the catheter. In an embodiment, the strain relief mechanism is located proximally outside of the catheter body (within the catheter connector and/or within the handle). The mechanism allows for a portion of the electrical cable slack to remain in the cable lumen, when the instrument is not bent. The mechanism is engaged during a cable strain condition, and the engaged mechanism biases the electrical cable toward the proximal end of the instrument. In one embodiment, the mechanism's motion is predominately linear (e.g., powered by a compression/extension spring). In an alternate embodiment, the mechanism's motion is predominately radial (e.g. powered by a torsion spring or cantilever arm). The linear motion or radial motion generated by the strain relief mechanism's motion exerts a tension force on the electrical cable in a range between 0.2 and 5.0 Newton, and more preferably a tension force of 1.0 Newton.

The electrical cable has a lubricious outer coating or membrane to provide accommodation for the cable during instrument steering and navigation. At least a portion of electrical cable has an outer jacket configured to enhance strain relief. The outer jacket of the electrical cable is provided at least in the distal end of the steerable section. At least a portion of the electrical cable conduit (wire-conduit) has a torsional modulus of 15 Gpa. At least a portion of the electrical cable conduit (wire-conduit 104) has a lubricious membrane or coating made of polyimide, PEEK or similar material.

<Electrical Cable Structure and Stress Profile of Strain Relief Elements>

In the foregoing embodiments, the electrical cable 112 is shown as a single element for ease of illustration and description. However, it should be understood, that the electrical cable 112 is not limited to a structure having a single element (i.e., a single strand). More specifically, as understood by persons skilled in the art, the electrical cable 112 can be comprised of one or more (e.g., two) conducting elements, including, for example, two electrical conducting wires (copper wires for conducting electricity). However, conducting elements are not limited to only wires. In the cable cross section, the wires are jacketed by a shrink tube material made of polyester, for example. This jacket material aides in the manufacture of the strain relief elements. The wires may be twisted in respect to another cable element, another wire for example. The twisted element may also be fused or coupled, at least partially, to another element.

Figure 15:
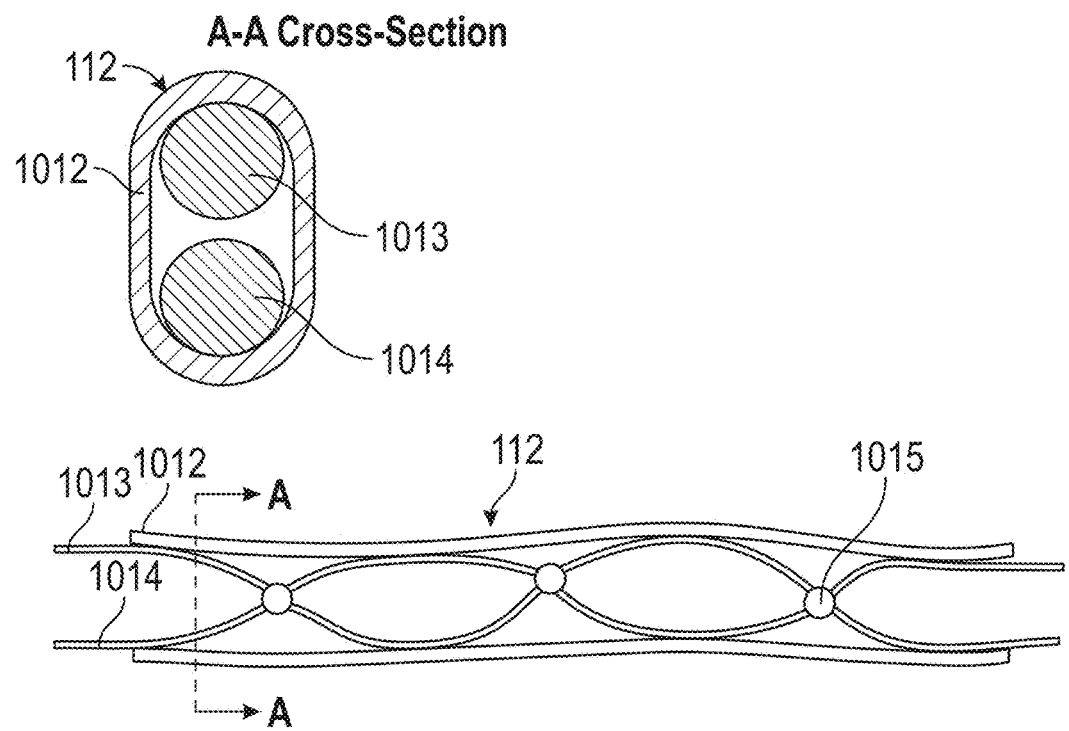
FIG. 15 shows examples of an electrical cable 112 formed by a plurality of wire strands.

FIG. 15 shows an example an electrical cable 112. In one example, the electrical cable 112 includes a jacket 1012, a first conducting element 1013 and a second conducting element 1014. At least one of these conducting elements 1013 or 1014 is twisted in respect to another element (may be the other wire, or the sheath, or other cable structure). In another example, the electrical cable 112 includes a twisted pair of wires fused together, at least partially, at predetermined points 1015. For an electrical cable 112 having one or more conducting elements enclosed in a jacket 1012, the jacket can be a low friction or lubricious membrane (e.g., made of polyimide or PEEK) covering at least a portion of the electrical cable. In another example, the electrical cable can be jacketed by polyester shrink tube, which greatly improves maneuverability and configuration of the strain relief portions. This jacketing can be particularly advantageous in the distal end of the steerable instrument 100 to minimize stress of the electrical cable during steering of the instrument.

Figure 16:
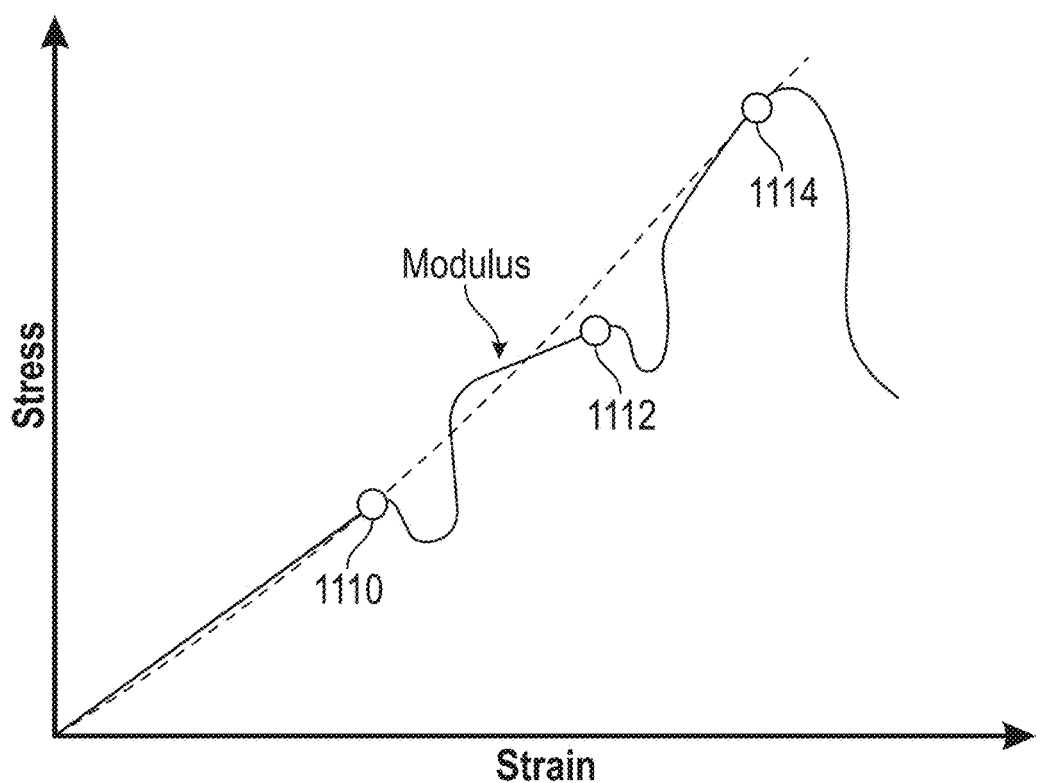
FIG. 16 illustrates a graph of a Young's Modulus for an electrical cable 112, according to the present disclosure.

FIG. 16 illustrates a graph of the Modulus (stress vs strain) for the electrical cable 112. In general, a stress-strain curve for a material gives the relationship between stress and strain. Stress is the force applied to a material, divided by the material's cross-sectional area, and strain is the deformation or displacement of material that results from the applied stress.

In the present disclosure, since the electrical cable 112 has multiple structural elements, twisted wires that are partially fused and heat shrink jacket for example, one or more linear regions may be observed in the cable's stress/strain curve. Specifically, the electrical cable 112 comprises one or more electrical conducting elements. Therefore, multiple strain yield points can be observed in the stress/strain curve (Modulus) of the cable. For example, for a cable 112 having only one strand (or a few strands) of electrical wire, of a section of the electrical cable 112, a first yield point (or point of failure) 1010 could be observed at relatively low stress/strain ratios. For a section of electrical cable 112 having a higher number of electrical wire strands or having multiple structures, a higher yield point 1112 can be expected. Overall, however, the modulus of the entire cable is expected to have a Young's Modulus of a yield point 1114, which is the highest modulus for which the cable is designed. Yield point 114 is that of a conductor made of copper wire core, for example.

Therefore, an additional benefit of the strain relief design is an improvement in the Young's Modulus of the cable assembly. The Young's Modulus property of the electrical cable 112 is particularly useful in the catheter extrusion body region where strain is low (lower than in the disk region). A typical value for Young's modulus of a copper wire is in the 130 Gpa region. In an exemplary application of the steerable instrument 100, this typical Young modulus of copper would yield a strain value of approximately 0.1% or 0.6 mm of elastic elongation for an EM sensor cable; this is based on a 550 mm catheter extrusion body length. However, under the design conditions described herein, experimental measurements of the cable assembly yields a Young's Modulus of 15 Gpa or a 0.85% strain value leading to 4.7 mm of elastic elongation.

Table 1 below shows a summary of the advantageous benefits of the strain relief design in terms cable elongation.

TABLE 1

| Strain Imparted To The EM Cable (Catheter Extrusion Body Region) | Strain Benefit Of Our EM Cable (Catheter Extrusion Body Region) | Strain Benefit Of Traditional Copper Wire (Catheter Extrusion Body Region) |
| --- | --- | --- |
| 1.2% 6.6 mm of wire elongation (550 mm Proximal Catheter Body Length) | .85% 4.7 mm of wire elongation (550 mm Proximal Catheter Body Length) | .1% .6 mm of wire elongation (550 mm Proximal Catheter Body Length) |

As already mentioned above, the strain relief of electrical cable 112 may be further improved by providing a lubricious outer coating or membrane to the cable. The outer jacket of the electrical cable can be provided at least in the distal end of the steerable section 103 of the steerable instrument 100. In addition, at least a portion of the wire-guiding members 408, in particular the wire conduit 104 and/or groove 512 (FIG. 6A-6E) which serves as a conduit for the electrical cable 112, can be covered with a lubricious membrane made of, for example, thermoplastic polyimide or polyetheretherketone (PEEK).

The foregoing embodiments describe a steerable instrument 100, such as tubular catheter body with at least one steerable section and one flexible but non-steerable section arranged along an axis from a distal end to a proximal end. The catheter body includes at least one tool channel, a plurality of control wires along the wall of the catheter body, and at least one electrical cable assembly having strain relief elements. In the catheter body, there is at least one "void" section that houses at least part of the electrical cable assembly such that the cable is not in substantial contact with other substructures of the catheter body. The electrical cable is at least partially routed circumferentially around the catheter's central axis (around the tool channel), so as to complete one or more revolutions. The electrical cable has a modulus in a range of 2-25 gigapascals (Gpa). The electrical cable 112 may include one or more electrical wires (strands of wire), and at least part of the cable's wires are wound in a braided like fashion. The electrical cable is affixed in at least one location to the catheter's structure along the catheter's length thereof. In one embodiment, affixing the electrical cable to the catheter structure can be done via bonding process. In other embodiment, the electrical cable is affixed to the catheter structure by routing the cable around substructures (rings or disks) of the catheter body such that friction between catheter body and cable portions exceeds a coefficient of friction value between 0.2 and 1. Affixing the electrical cable to the catheter structure is also achieved by at least partially "looping" the electrical cable around the catheters structure with minimum contact therebetween. According to one embodiment, the electrical cable is looped around a void region of the catheter, and is routed between neighboring void regions through a groove formed on the outer surface of the catheter structure, such that the cable does not increase the outside diameter of the catheter structure. During actuation of the steerable section, one localized region of cable strain can pull slack from at least one other non-strained region of the electrical cable. The cable is routed such that at least one substructure of the catheter is inhibited from protruding beyond the catheters outside diameter. The cable is routed such that at least one of the control wires is inhibited from prolapsing. In at least the non-steerable section of the catheter, the cable is routed such that at least part of the cable is offset from the catheters central axis of the catheter.

The disclosure also provides an electrical cable having a plurality of strain relief features and a plurality of guide features for a portion of the electrical cable disposed in the steerable portion of a steerable instrument, such as a robotic catheter or endoscope. The strain relief features described in this disclosure provide enhanced catheter articulation while minimizing the catheter diameter and reducing strain on the catheter body. Improved strain relief for catheter manipulation is achieved by, for example, arranging portions of an electrical cable in void regions of the catheter so that the electrical cable does not have meaningful contact with other catheter substructures. This results in low strain forces being transmitted to the electrical cable via minimized contact surface area. The particular arrangement of the electrical cable in void regions of the steerable section provides a mechanism that blocks the transmission of strain force from the proximal region to the distal region and vice versa. This provides enhanced strain relief and a safety factor because the electrical cable can block unintended or stray forces from damaging the EM sensor leads. The steerable section of the catheter body is bent, twisted, and/or rotated by driving one or more control wires arranged along the length of the catheter body. Since the contact of the electrical cable with the other catheter structures are minimized, enhanced catheter articulation is advantageously achieved. Arranging the electrical cable in catheter void regions, such that the cable loops around the control wires, reduces incidence of drive wire prolapse while maintaining a minimized catheter outer diameter. The strain relief assembly requires a cable structure with a Young's Modulus of about 15 Gpa (Table 1). With these parameters, the electrical cable is able to withstand at least 0.85% elastic deformation, which results in a 4.7 mm strain relief relative to a 550 mm length. This is considered an important design feature as this enables the electrical cable to elongate without breaking or straining other catheter structures under strain conditions. Routing the electrical cable through a groove formed in the circumference of the wire-guiding members allows for the electrical cable to be arranged with minimal contact and within the catheter's outer surface without increasing the diameter.

In general, an advantage of the present strain relief design is that the electrical cable can adapt to different geometrical conditions of the steerable instrument, and still maintain states of non-stress or minimal stress throughout the cable. Further, when the steerable instrument is in a state of extreme tortuosity, the strain relief allows the electrical cable to elongate without restricting catheter articulation, while simultaneously avoiding a potential open circuit condition. This is enabled by the unique arrangement of the electrical cable within void regions of the catheter body and by appropriate modulus summarized in Table 1.

In referring to the above description, specific details are set forth in order to provide a thorough understanding of the embodiments disclosed. In other instances, well-known methods, procedures, components and circuits have not been described in detail as not to unnecessarily lengthen the present disclosure. Unless defined otherwise herein, all technical and scientific terms used herein have the same meaning as commonly understood by one of ordinary skill in the art to which this disclosure belongs. The breadth of the present disclosure is not to be limited by the subject specification, but rather only by the plain meaning of the claim terms employed.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the scope of the following claims is to be accorded the broadest reasonable interpretation so as to encompass all modifications and equivalent structures and functions.

The invention claimed is:

1. A robotically steerable medical instrument, comprising:
a catheter body having a proximal section configured to be mechanically coupled to an actuator system and a distal section configured to be actuated by the actuator system, the catheter body defining a tool channel which extends along a central axis from a proximal end to a distal end of the catheter body and having plural control wires and at least one electrical cable arranged lengthwise along a wall of the catheter body,
wherein the control wires link the distal section to the actuator system and are configured to transfer an actuating force from the actuator system to the distal section of the catheter body so as to bend at least a portion of the distal section,
wherein the distal section includes a plurality of wire-guiding members arranged at a predetermined distance from each other so as to form a plurality of void regions alternately interposed with the plurality of wire-guiding members in the lengthwise direction of the catheter body,
wherein the electrical cable configured to establish an electrical connection between an electrical circuit located outside the catheter body and an electronic component arranged at the distal end or within the distal section of the catheter body, and
wherein the electrical cable includes strain relief elements arranged in one or more void regions such that when the electrical cable is subjected to a tensile load by the actuating force bending the distal section of the catheter body, the strain relief elements within the one or more void regions minimize the tensile load on the electrical cable.

2. The robotically steerable medical instrument according to claim 1,
wherein the strain relief elements include first portions of the electrical cable which are loosely arranged within the one or more void regions such that, within the one or more void regions, the first portions of the electrical cable can freely move, slide, and/or tighten in response to the actuating force bending the distal section to thereby provide strain relief to, or minimize the tensile load of, the electrical cable.

3. The robotically steerable medical instrument according to claim 2,
wherein, within the one or more the void regions, the first portions of the electrical cable are coiled around the tool channel or folded along the lengthwise direction outside of the tool channel.

4. The robotically steerable medical instrument according to claim 2,
wherein the proximal section of the catheter body is a non-steerable section formed of a hollow shaft having shaft wall between an inner surface and an outer surface, and
wherein the hollow shaft includes a plurality of wire conduits arranged in the shaft wall equidistantly from the central axis in a lengthwise direction thereof.

5. The robotically steerable medical instrument according to claim 4,
wherein the distal section is a steerable section actuatable by the plurality of control wires, and
wherein the plurality of wire-guiding members alternated with the plurality of void regions are arranged distally to the hollow shaft.

6. The robotically steerable medical instrument according to claim 5,
wherein each of the plurality of wire-guiding members has a central opening concentric with the central axis and enclosed by a wall, and the wall of each wire-guiding member includes a plurality of wire conduits formed between an inner surface and an outer surface thereof, and
wherein a first control wire is arranged along a first wire conduit in the hollow shaft and along a first wire conduit in one or more wire-guiding members.

7. The robotically steerable medical instrument according to claim 6,
wherein the one or more wire-guiding members include a groove along the wall thereof,
wherein the electrical cable is guided from the proximal end of the catheter body to the distal section by passing the electrical cable through a second wire conduit within the shaft wall, and arranging the electrical cable alternately along the wall of the one or more wire-guiding members and the one or more void regions.

8. The robotically steerable medical instrument according to claim 7,
wherein the electrical cable is routed from one void region to another void region through the groove along the wall of the one or more wire-guiding members, and
wherein the electrical cable and the groove are dimensioned so as to route the electrical cable through the groove without increasing an outer dimension of the catheter body.

9. The robotically steerable medical instrument according to claim 8,
wherein the groove is formed on the outer surface or the inner surface of the wall of the one or more wire-guiding members, and
wherein the groove is slanted or parallel with respect to the lengthwise direction of the outer surface of the one or more wire-guiding members.

10. The robotically steerable medical instrument according to claim 8,
wherein the groove is formed as cut joining the outer surface to the inner surface of the wall of the one or more wire-guiding members, and
wherein the cut is slanted or parallel with respect to the lengthwise direction of the inner surface and the outer surface of the one or more wire-guiding members.

11. The robotically steerable medical instrument according to claim 7, further comprising:
an inner sheath made of polymer material and/or woven fibers and configured to enclose at least part of the tool channel,
wherein the one or more wire-guiding members and the void regions interposed with the one or more wire-guiding members are arranged around the inner sheath,
wherein both the electrical cable and the control wires surround the inner sheath,
wherein the one or more wire-guiding members are attached to the inner sheath by reflowing material of the wire-guiding members and/or material of the inner sheath onto each other, and wherein the electrical cable is guided from one void region to another void region between the outer surface of the inner sheath and the inner surface of the one or more wire-guiding members.

12. The robotically steerable medical instrument according to claim 7, further comprising:
an outer sheath made of polymer material and/or woven fibers and configured to enclose at least part of the distal section of the catheter body,
wherein the outer sheath encloses the one or more wire-guiding members and the void regions interposed with the one or more wire-guiding members,
wherein the outer sheath surrounds both the electrical cable and the control wires within the void regions interposed with the one or more wire-guiding members, and
wherein, when the tensile load by the actuating force bends the distal section of the catheter body, the outer sheath is configured to prevent prolapse of the electrical cable and/or control wires within the void regions interposed with the one or more wire-guiding members.

13. The robotically steerable medical instrument according to claim 2,
wherein one or more second portions of the electrical cable is affixed to one or more locations along the proximal section and/or along the distal section of the catheter body, and
wherein, when the distal section is bent by the actuating force, at least one of the one or more second portions of the electrical cable does not slide with respect to at least one of the proximal section and the distal section of the catheter body.

14. The robotically steerable medical instrument according to claim 13,
wherein the one or more second portions of the electrical cable is affixed to one or more wire-guiding members along the distal section of the catheter body such that the electrical cable does not slide with respect to at least one wire-guiding member.

15. The robotically steerable medical instrument according to claim 5,
wherein the first portions of the electrical cable are arranged in the one or more void regions looped or wrapped around the tool channel from at least a partial revolution to multiple revolutions.

16. The robotically steerable medical instrument according to claim 15,
wherein, within the one or more void regions, the first portions of the electrical cable are looped or wrapped around the tool channel and routed over the control wires or under the control wires or alternately over and under the control wires.

17. The robotically steerable medical instrument according to claim 5,
wherein a first control wire among the plurality of control wires is arranged in a first wire conduit of the shaft wall and the electrical cable is arranged in a second wire conduit of the shaft wall such that both the first control wire and the electrical cable pass through the length of the hollow shaft through separate wire conduits.

18. The robotically steerable medical instrument according to claim 17,
wherein each of the wire-guiding members is a ring-shaped wire-guiding member having an inner diameter and an outer diameter, and each of the wire-guiding members includes a plurality of wire conduits formed lengthwise in an annular wall of each wire-guiding member between the inner surface and the outer surface thereof, and
wherein a first wire-guiding member of the steerable section is either attached to the distal end of the hollow shaft or arranged at a distance from the distal end of the hollow shaft.

19. The robotically steerable medical instrument according to claim 18,
wherein the first control wire passes from the distal end of the hollow shaft to the first wire-guiding member and advances through a wire conduit of the first wire-guiding member substantially parallel to the central axis of the catheter body, and the electrical cable is routed along a groove formed on the annular wall of the first wire-guiding member at an angle with respect to the central axis, and
wherein at least one of the first portions of the electrical cable is arranged in at least one void region among the plurality of the void regions such that, within the at least one void region, the electrical cable is not in substantial contact with other substructures of the catheter body.

20. The robotically steerable medical instrument according to claim 1,
wherein the electrical cable is made of one or more strands of electrically conducing wire,
wherein at least part of the one or more strands of electrical conducting wire are wound into a twisted pair cable or weaved into a braided multi-strand cable such that the electrical cable has an average Young's modulus in a range of 2-25 gigapascals.

21. The robotically steerable medical instrument according to claim 1,
wherein the electrical cable is affixed to a first location of the catheter body by attaching the electrical cable to an anchoring point in the proximal section and/or distal section of the catheter body,
wherein the electrical cable is arranged along the distal section of the catheter body by guiding the electrical cable through one or more of the wire-guiding members offset from the central axis, and
wherein, in response to the actuating force bending the distal section, a strained portion of the electrical cable within a void region is configured to pull slack of an unstrained portion of electrical cable from at least one neighboring void region to thereby provide strain relief to, or minimize the tensile load of, the electrical cable.

22. The robotically steerable medical instrument according to claim 1,
wherein the electrical cable is routed between two or more consecutive void regions through an open lumen formed on a wall of each wire-guiding member such that a portion of the electrical cable connecting each pair of consecutive void regions is affixed to the wall of the wire-guiding member without increasing an outer diameter of the catheter body.

23. The robotically steerable medical instrument according to claim 1, further comprising:
a strain relief mechanism connected to the electrical cable and configured to add and/or remove electrical cable slack from within the catheter body,
wherein the strain relief mechanism is located in or connected to the proximal end of the catheter body proximally outside of the proximal section, wherein, when the distal section is not bent, the strain relief mechanism allows for a portion of the electrical cable slack to remain within the catheter body, and wherein, when the distal section is bent, the strain relief mechanism is configured to bias the electrical cable toward the proximal end of the catheter body so as to remove a portion of the electrical cable slack proportionally to an amount of bending of the proximal section.

24. The robotically steerable medical instrument according to claim 1, wherein the electrical component includes one or more electromagnetic (EM) sensors arranged along the distal section of the catheter body, and wherein the actuating force transferred by the one or more control wires bends the distal section to a curvature having a radius of about 5 mm without imparting substantial strain to the one or more EM sensors.

25. The robotically steerable medical instrument according to claim 1, wherein the proximal section has a first length L1 and the distal section has a second length L2, and the first length L1 is about 10 to 20 times longer than the second length L2, wherein each wire-guiding member has a length T measured in the lengthwise direction and each void region has a length P measured in the lengthwise direction, and wherein, in the distal section, the plurality of void regions and the plurality of wire-guiding members are alternately arranged in the lengthwise direction of the catheter body such that a ratio of the length T of each wire-guiding member to the length P of each void region is in a range of 0.5 and 1.0 inclusive.

* * * * *